(12) United States Patent
Kikitsu et al.

(10) Patent No.: US 12,270,866 B2
(45) Date of Patent: Apr. 8, 2025

(54) MAGNETIC SENSOR AND INSPECTION DEVICE

(71) Applicant: KABUSHIKI KAISHA TOSHIBA, Tokyo (JP)

(72) Inventors: Akira Kikitsu, Yokohama Kanagawa (JP); Yoshihiro Higashi, Komatsu Ishikawa (JP); Satoshi Shirotori, Yokohama Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 129 days.

(21) Appl. No.: 18/166,532

(22) Filed: Feb. 9, 2023

(65) Prior Publication Data

US 2024/0053414 A1  Feb. 15, 2024

(30) Foreign Application Priority Data

Aug. 9, 2022  (JP) .................................. 2022-127070

(51) Int. Cl.
  *G01R 33/00* (2006.01)
  *G01R 33/06* (2006.01)
(52) U.S. Cl.
  CPC ....... *G01R 33/0023* (2013.01); *G01R 33/063* (2013.01)
(58) Field of Classification Search
  None
  See application file for complete search history.

(56) References Cited

U.S. PATENT DOCUMENTS

| 2013/0008022 | A1* | 1/2013 | Yao ........................ G01R 33/09 29/830 |
| 2017/0363606 | A1 | 12/2017 | Kikitsu et al. |
| 2019/0242957 | A1* | 8/2019 | Furuichi ................ G01R 33/06 |
| 2019/0293735 | A1* | 9/2019 | Ushioda ................ G01R 33/02 |
| 2019/0369172 | A1 | 12/2019 | Kikitsu et al. |
| 2022/0065955 | A1 | 3/2022 | Kikitsu et al. |

FOREIGN PATENT DOCUMENTS

| JP | 2019-207167 A | 12/2019 |
| JP | 6668176 B2 | 3/2020 |
| JP | 2022-37688 A | 3/2022 |

* cited by examiner

*Primary Examiner* — Jas A Sanghera
(74) *Attorney, Agent, or Firm* — Finnegan, Henderson, Farabow, Garrett & Dunner, LLP

(57) ABSTRACT

According to one embodiment, a magnetic sensor includes an element portion and a conductive layer. The element portion includes a first magnetic element, a second magnetic element, a first conductive member, and a second conductive member. The first magnetic element includes a first end portion and a first other end portion. The second magnetic element includes a second end portion and a second other end portion. The first conductive member includes a first portion and a first other portion. The first portion corresponds to the first end portion. The first other portion corresponds to the first other end portion. The second conductive member includes a second portion and a second other portion. The second portion corresponds to the second end portion. The second other portion corresponds to the second other end portion. The conductive layer includes a first conductive portion and a first other conductive portion.

21 Claims, 13 Drawing Sheets

MAGNETIC SENSOR AND INSPECTION DEVICE

CROSS-REFERENCE TO RELATED APPLICATIONS

This application is based upon and claims the benefit of priority from Japanese Patent Application No. 2022-127070, filed on Aug. 9, 2022; the entire contents of which are incorporated herein by reference.

FIELD

Embodiments described herein generally relate to a magnetic sensor and an inspection device.

BACKGROUND

There is a magnetic sensor using a magnetic layer. There is an inspection device using a magnetic sensor. Magnetic sensors are desired to operate stably.

DETAILED DESCRIPTION

Figure 1:
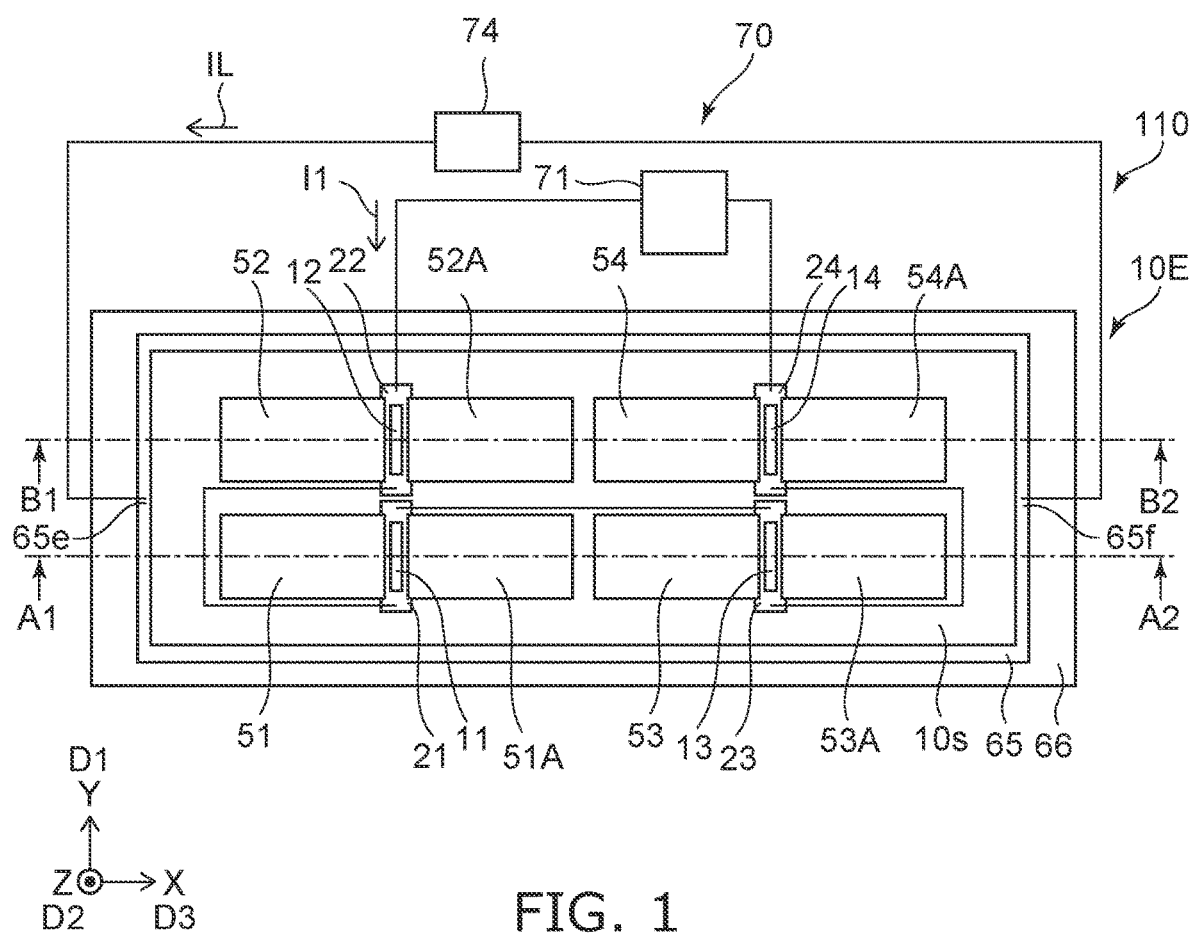
FIG. 1 is a schematic view illustrating a magnetic sensor according to a first embodiment.

According to one embodiment, a magnetic sensor includes an element portion and a conductive layer. The element portion includes a first magnetic element, a second magnetic element, a first conductive member, and a second conductive member. The first magnetic element includes a first end portion and a first other end portion. A direction from the first end portion to the first other end portion is along a first direction. The second magnetic element includes a second end portion and a second other end portion. A direction from the second end portion to the second other end portion is along the first direction. The second end portion is electrically connected to the first other end portion. The first conductive member includes a first portion and a first other portion. The first portion corresponds to the first end portion. The first other portion corresponds to the first other end portion. The second conductive member includes a second portion and a second other portion. The second portion corresponds to the second end portion. The second other portion corresponds to the second other end portion. A second direction from the conductive layer to the element portion crosses the first direction. The conductive layer includes a first conductive portion and a first other conductive portion. A third direction from the first conductive portion to the first other conductive portion crosses a plane including the first direction and the second direction.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously in an antecedent drawing are marked with like reference numerals, and a detailed description is omitted as appropriate.

First Embodiment

Figure 2:
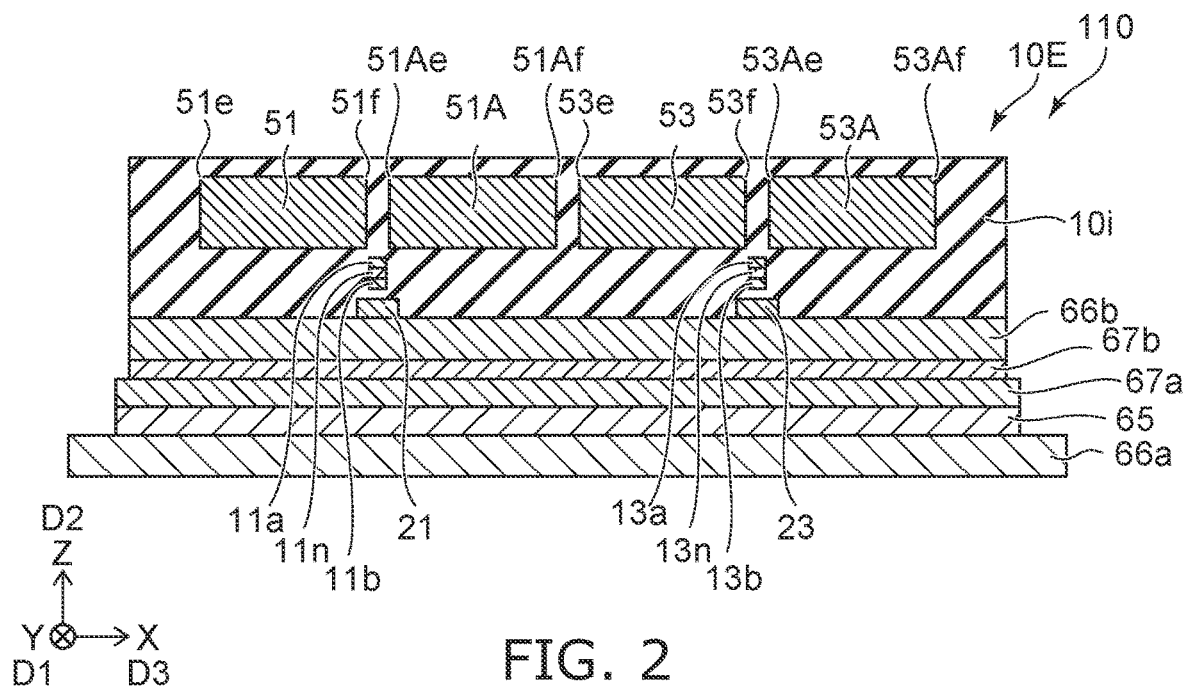
FIG. 2 is a schematic view illustrating the magnetic sensor according to the first embodiment.
Figure 3:
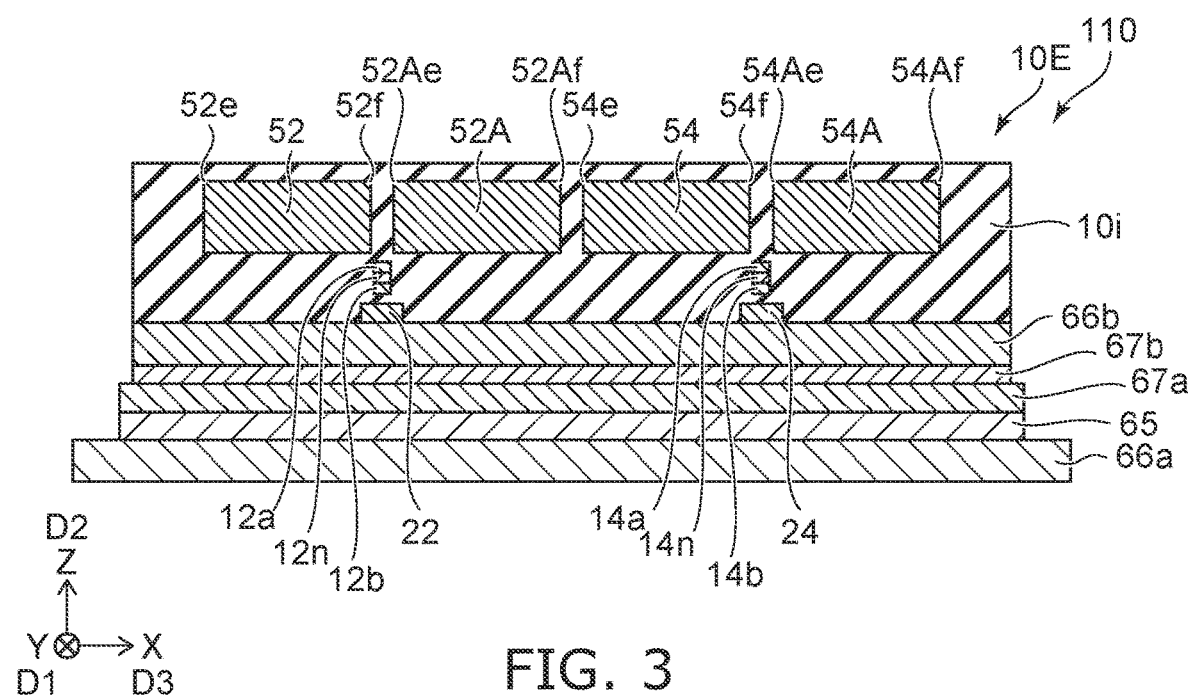
FIG. 3 is a schematic view illustrating the magnetic sensor according to the first embodiment.

FIGS. 1 to 3 are schematic views illustrating a magnetic sensor according to the first embodiment.

FIG. 1 is a plan view. FIG. 2 is a cross-sectional view taken along the line A1-A2 of FIG. 1. FIG. 3 is a cross-sectional view taken along the line B1-B2 of FIG. 1.

Figure 4A:
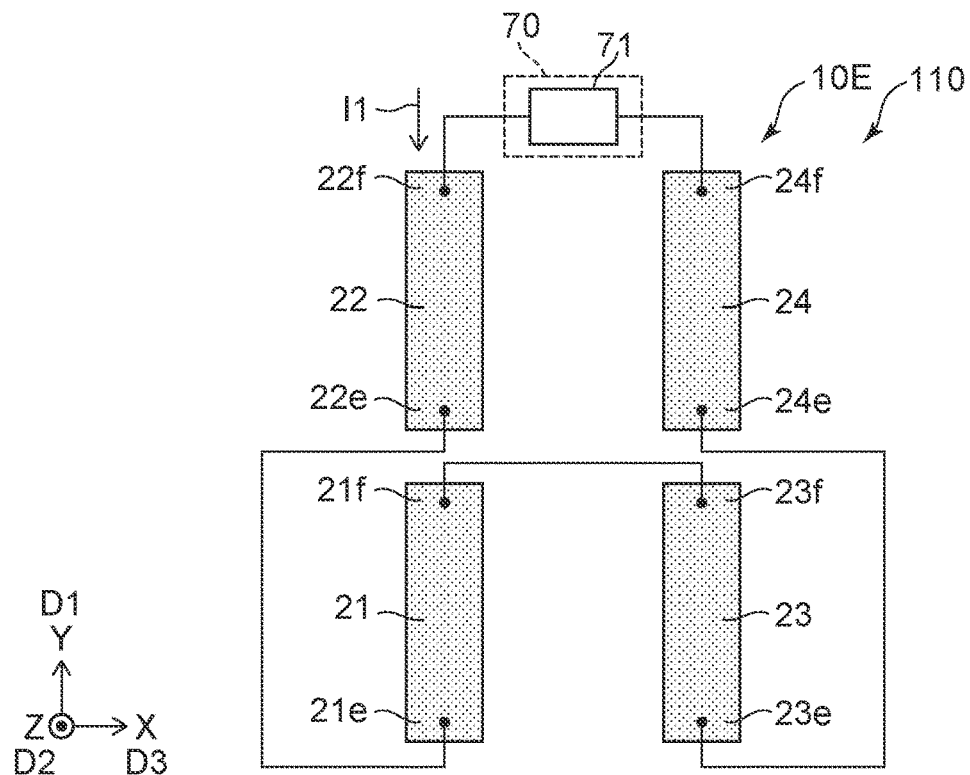
FIGS. 4A and 4B are schematic plan views illustrating the magnetic sensor according to the first embodiment.
Figure 4B:
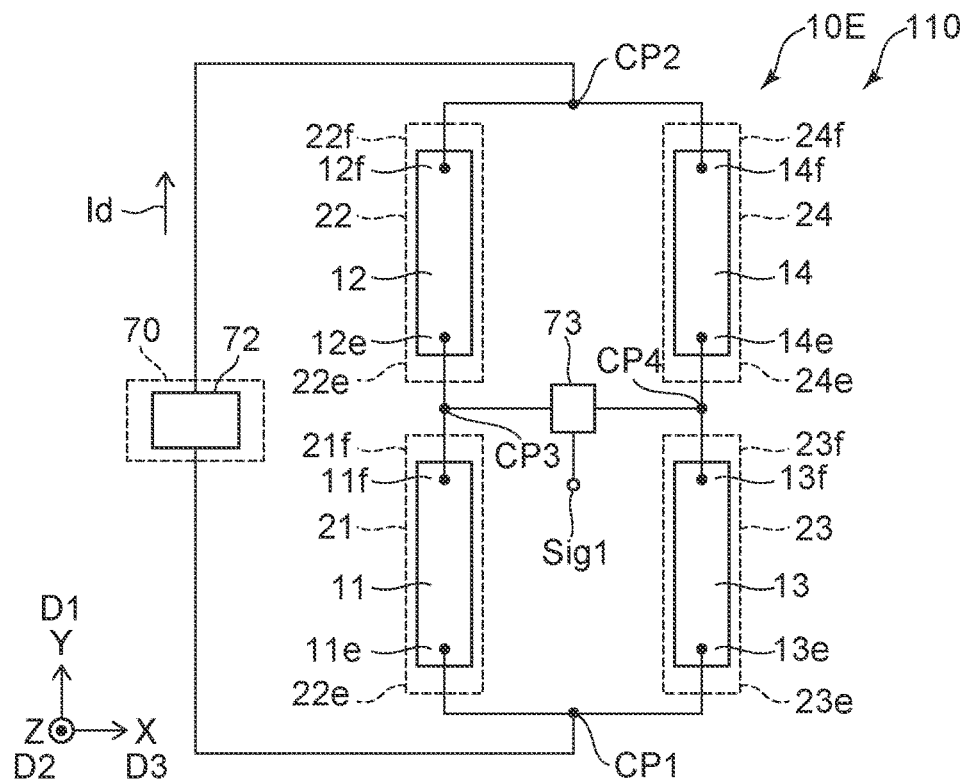

FIGS. 4A and 4B are schematic plan views illustrating the magnetic sensor according to the first embodiment.

As shown in FIGS. 1 to 3, a magnetic sensor 110 according to the embodiment includes an element portion 10E and a conductive layer 65. The element portion 10E includes a first magnetic element 11, a second magnetic element 12, a first conductive member 21 and a second conductive member 22. In this example, the element portion 10E includes a third magnetic element 13, a fourth magnetic element 14, a third conductive member 23, and a fourth conductive member 24. The third magnetic element 13, the fourth magnetic element 14, the third conductive member 23, and the fourth conductive member 24 will be described later.

FIG. 4A illustrates the first conductive member 21, the second conductive member 22, the third conductive member 23, and the fourth conductive member 24. FIG. 4B illustrates the first magnetic element 11, the second magnetic element 12, the third magnetic element 13, and the fourth magnetic element 14.

As shown in FIG. 4B, the first magnetic element 11 includes a first end portion 11e and a first other end portion 11f. A direction from the first end portion 11e to the first other end portion 11f is along the first direction D1.

The first direction D1 is defined as a Y-axis direction. One direction perpendicular to the Y-axis direction is defined as a Z-axis direction. The direction perpendicular to the Y-axis direction and the Z-axis direction is defined as an X-axis direction.

As shown in FIG. 4B, the second magnetic element 12 includes a second end portion 12e and a second other end portion 12f. A direction from the second end portion 12e to the second other end portion 12f is along the first direction D1. The second end portion 12e is electrically connected to the first other end portion 11f.

As shown in FIGS. 4A and 4B, the first conductive member 21 includes a first portion 21e and a first other portion 21f. The first portion 21e corresponds to the first end portion 11e. The first other portion 21f corresponds to the first other end portion 11f.

As shown in FIGS. 4A and 4B, the second conductive member 22 includes a second portion 22e and a second other portion 22f. The second portion 22e corresponds to the second end portion 12e. The second other portion 22f corresponds to the second other end portion 12f.

As shown in FIGS. 2 and 3, a second direction D2 from the conductive layer 65 to the element portion 10E crosses the first direction D1. The second direction D2 is, for example, the Z-axis direction.

As shown in FIG. 1, the conductive layer 65 includes a first conductive portion 65e and a first other conductive portion 65f. A third direction D3 from the first conductive portion 65e to the first other conductive portion 65f crosses a plane including the first direction D1 and the second direction D2. The third direction D3 is, for example, the X-axis direction.

In the embodiment, the first electrical resistance of the first magnetic element 11 and the second electrical resistance of the second magnetic element 12 change according to a magnetic field of the detection target. This is because the magnetic field of the detection target changes the magnetization direction of the magnetic layers included in these magnetic elements. In the embodiment, the first current I1 including an AC component is supplied to the first conductive member 21 and the second conductive member 22. A magnetic field (alternating magnetic field) generated by the first current I1 is applied to the first magnetic element 11 and the second magnetic element 12. The electrical resistance of these magnetic elements also changes depending on the magnetic field (alternating magnetic field) generated by the first current I1. By detecting the signals corresponding to the electrical resistances of these magnetic elements using the alternating signal from the first current I1 as a reference, noise can be suppressed and magnetic field of the detection target can be detected with high accuracy.

For example, the magnetic properties of the element portion 10E may be changed by an unintended surrounding magnetic field. For example, the magnetic sensor 110 may unintentionally be brought to near to a magnetic material, and then the magnetization of its magnetic layer in the magnetic element may be changed. For example, magnetic domains may be generated in the magnetic layer may by an unintended operation. In such cases, the magnetic properties of the magnetic element may change, and the desired detection capability is difficult to be achieved.

In the embodiments, the conductive layer 65 is provided. A current is supplied to the conductive layer 65. The magnetization of the magnetic layer included in the magnetic element is initialized to a desired state by the magnetic field generated by the current. This makes stable detection possible. According to an embodiment, a magnetic sensor capable of stable operation can be provided.

As shown in FIG. 1, a current circuit 74 and a first circuit 71 may be provided. The current circuit 74 and the first circuit 71 may be included in magnetic sensor 110. The current circuit 74 is configured to supply a conductive layer current IL to the conductive layer 65. The first circuit 71 is configured to supply the first current I1 to the first conductive member 21 and the second conductive member 22.

As shown in FIG. 4B, a second circuit 72 and a third circuit 73 may be provided. The second circuit 72 and the third circuit 73 may be included in the magnetic sensor 110. The second circuit 72 is configured to supply an element current Id (or element voltage) to the first magnetic element 11 and the second magnetic element 12. The third circuit 73 is configured to detect values corresponding to the first electrical resistance of the first magnetic element 11 and the second electrical resistance of the second magnetic element 12.

An example of the operation of these circuits will be described below.

Figure 5A:
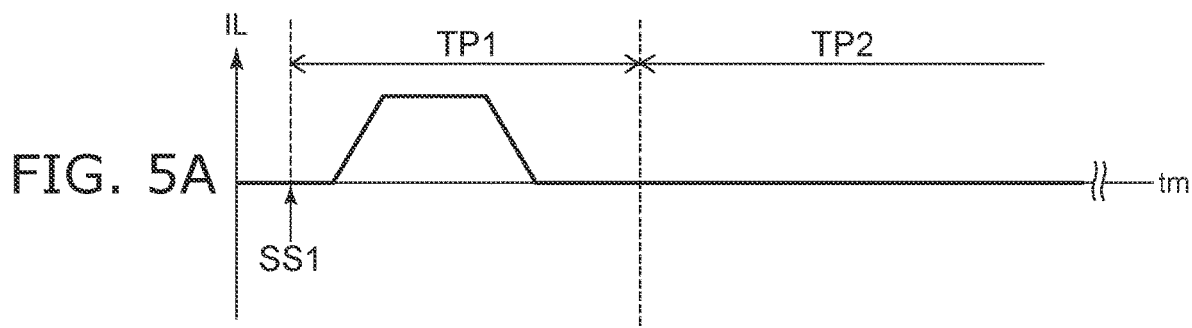
FIGS. 5A to 5C are schematic diagrams illustrating operations of the magnetic sensor according to the first embodiment.
Figure 5B:
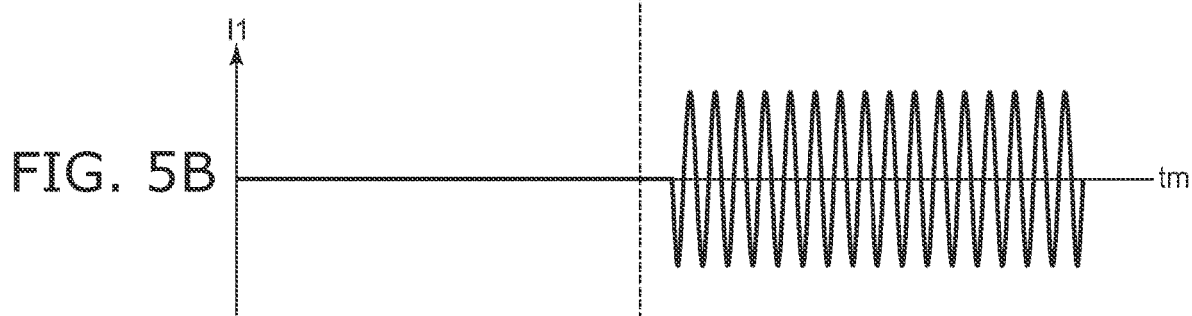
Figure 5C:
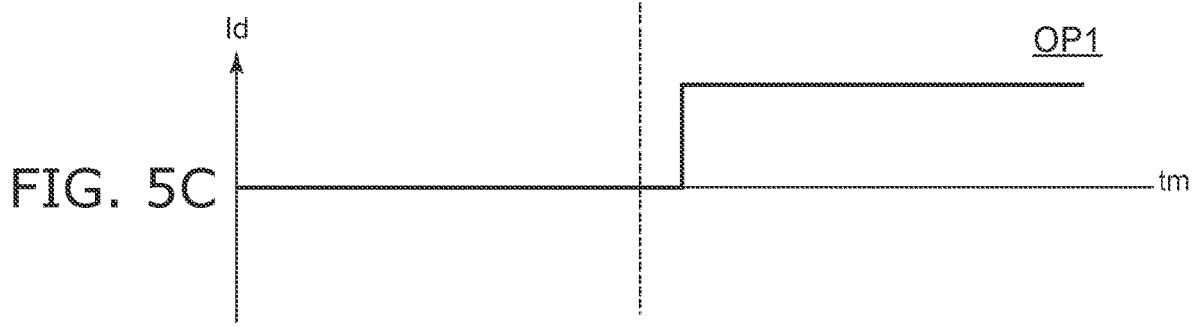

FIGS. 5A to 5C are schematic diagrams illustrating operations of the magnetic sensor according to the first embodiment.

The horizontal axis of these figures is time tm. The vertical axis of FIG. 5A represents the conductive layer current IL. The vertical axis of FIG. 5B represents the first current I1. The vertical axis of FIG. 5C represents the element current Id.

As shown in FIG. 5A, a first period TP1 and a second period TP2 can be set. The first period TP1 is, for example, an initialization period. The first period TP1 is, for example, a refresh period. The second period TP2 is a detection period. The first period TP1 may be started by, for example, an initialization start signal SS1 from the outside. Alternatively, the first period TP1 may be started at a predetermined time or the like. The length of the first period TP1 can be set.

As shown in FIG. 5A, the current circuit 74 can supply the conductive layer current IL to the conductive layer 65 in the first period TP1. As shown in FIG. 1, the conductive layer current IL flows between the first conductive portion 65e and the first other conductive portion 65f. The direction of the conductive layer current IL is along the third direction D3.

As shown in FIG. 5A, the conductive layer current IL is substantially 0 in the second period TP2. The current circuit 74 does not supply the conductive layer current IL between the first conductive portion 65e and the first other conductive portion 65f in the second period TP2. The magnitude of the conductive layer current IL in the second period TP2 is 1/10 or less of the magnitude of the conductive layer current IL in the first period TP1.

As shown in FIG. 5B, the first current I1 flows in the second period TP2. As shown in FIG. 4A, the first current I1 passes through the first conductive member 21 and the second conductive member 22. In this manner, the first circuit 71 can supply the first current I1 including the AC component to the first conductive member 21 and the second conductive member 22 in the second period TP2.

As shown in FIG. 5B, the first circuit 71 does not supply the first current I1 to the first conductive member 21 and the second conductive member 22 in the first period TP1. For example, the magnitude of the first current I1 in the first period TP1 is 1/10 or less of the magnitude of the first current I1 in the second period TP2.

In the first period TP1 in which the conductive layer current IL is supplied, for example, initialization is performed. The detection operation is performed in the second period TP2 in which the first current I1 is supplied.

As shown in FIG. 5C, the second circuit 72 and the third circuit 73 are configured to perform the detection operation OP1 in the second period TP2. In the detection operation OP1, the second circuit 72 supplies the element current Id (or element voltage) to the first magnetic element 11 and the second magnetic element 12.

In the detection operation OP1, the third circuit 73 is configured to detect a signal (detection signal Sig1) corresponding to the difference between the first electrical resistance of the first magnetic element 11 and the second electrical resistance of the second magnetic element 12.

As shown in FIG. 5C, the second circuit 72 and the third circuit 73 do not perform the detection operation OP1 in the first period TP1. For example, the magnitude of the element current Id in the first period TP1 is $\frac{1}{10}$ or less of the element current Id in the second period TP2.

By performing the detection operation OP1 after the first period TP1 (refresh period), a stable operation can be achieved in the detection operation OP1.

A combination of the first period TP1 and the second period TP2 may be provided repeatedly. The first period TP1 may be provided before the second period TP2.

The first circuit 71, the second circuit 72, the third circuit 73 and the current circuit 74 may be included in the circuit portion 70.

As shown in FIG. 4B, for example, the element current Id flows from the first other end portion 11f to the first end portion 11e. The element current Id flows from the second other end portion 12f to the second end portion 12e.

As shown in FIG. 4A, for example, the second portion 22e is electrically connected to the first portion 21e. The first current I1 flows, for example, from the second other portion 22f to the second portion 22e and from the first portion 21e to the first other portion 21f. When the first current I1 flows from the second other portion 22f to the second portion 22e, the first current I1 flows from the first portion 21e to the first other portion 21f. The phase of the current flowing through the first conductive member 21 is opposite to the phase of the current flowing through the second conductive member 22. As a result, the direction of the magnetic field generated by the first current I1 to the first magnetic element 11 is opposite to the direction of the magnetic field generated by the first current I1 to the second magnetic element 12. Noise is suppressed by detecting the difference in the electrical resistance of these magnetic elements. Detection with higher sensitivity is possible.

As shown in FIGS. 1 to 3, in this example, the element portion 10E further includes a third magnetic element 13, a fourth magnetic element 14, a third conductive member 23, and a fourth conductive member 24.

As shown in FIG. 4B, the third magnetic element 13 includes a third end portion 13e and a third other end portion 13f. A direction from the third end portion 13e to the third other end portion 13f is along the first direction D1. The third end portion 13e is electrically connected to the first end portion 11e.

The fourth magnetic element 14 includes a fourth end portion 14e and a fourth other end portion 14f. A direction from the fourth end portion 14e to the fourth other end portion 14f is along the first direction D1. The fourth end portion 14e is electrically connected to the third other end portion 13f. The fourth other end portion 14f is electrically connected to the second other end portion 12f.

As shown in FIGS. 4A and 4B, the third conductive member 23 includes a third portion 23e and a third other portion 23f. The third portion 23e corresponds to the third end portion 13e. The third other portion 23f corresponds to the third other end portion 13f.

As shown in FIGS. 4A and 4B, the fourth conductive member 24 includes a fourth portion 24e and a fourth other portion 24f. The fourth portion 24e corresponds to the fourth end portion 14e. The fourth other portion 24f corresponds to the fourth other end portion 14f.

As shown in FIG. 4A, the first circuit 71 is electrically connected to the second other portion 22f and the fourth other portion 24f. The first circuit 71 is configured to supply the first current I1 to the third conductive member 23 and the fourth conductive member 24 in the second period TP2.

As shown in FIG. 4B, the second circuit 72 is electrically connected to a first connection point CP1 of the first end portion 11e and the third end portion 13e, and a second connection point CP2 of the second other end portion 12f and the fourth other end portion 14f. In the detection operation OP1, the second circuit 72 supplies the element current Id (or element voltage) between the first connection point CP1 and the second connection point CP2. For example, the element current Id flows from the third other end portion 13f to the third end portion 13e. The element current Id flows from the fourth other end portion 14f to the fourth end portion 14e.

A bridge circuit (a so-called full bridge circuit) is formed by the first magnetic element 11, the second magnetic element 12, the third magnetic element 13 and the fourth magnetic element 14. The use of the bridge circuit enables higher accuracy detection.

As shown in FIG. 4B, the third circuit 73 is electrically connected to a third connection point CP3 of the first other end portion 11f and the second end portion 12e, and a fourth connection point CP4 of the third other end portion 13f and the fourth end portion 14e. The third circuit 73 is configured to detect the detection signal Sig1 corresponding to the potential difference between the third connection point CP3 and the fourth connection point CP4 in the detection operation OP1.

As shown in FIG. 2, the first magnetic element 11 includes, for example, a first magnetic layer 11a, a first opposing magnetic layer 11b, and a first non-magnetic layer 11n. A direction from the first opposing magnetic layer 11b to the first magnetic layer 11a is along the second direction D2. The first non-magnetic layer 11n is between the first opposing magnetic layer 11b and the first magnetic layer 11a.

As shown in FIG. 3, the second magnetic element 12 includes, for example, a second magnetic layer 12a, a second opposing magnetic layer 12b and a second non-magnetic layer 12n. A direction from the second opposing magnetic layer 12b to the second magnetic layer 12a is along the second direction D2. The second non-magnetic layer 12n is between the second opposing magnetic layer 12b and the second magnetic layer 12a. As shown in FIG. 2, the third magnetic element 13 includes, for example, a third magnetic layer 13a, a third opposing magnetic layer 13b and a third non-magnetic layer 13n. A direction from the third opposing magnetic layer 13b to the third magnetic layer 13a is along the second direction D2. The third non-magnetic layer 13n is between the third opposing magnetic layer 13b and the third magnetic layer 13a.

As shown in FIG. 3, the fourth magnetic element 14 includes, for example, a fourth magnetic layer 14a, a fourth opposing magnetic layer 14b and a fourth non-magnetic layer 14n. A direction from the fourth opposing magnetic layer 14b to the fourth magnetic layer 14a is along the second direction D2. The fourth non-magnetic layer 14n is between the fourth opposing magnetic layer 14b and the fourth magnetic layer 14a.

One of the first magnetic layer 11a and the first opposing magnetic layer 11b may be a magnetization free layer. The other of the first magnetic layer 11a and the first opposing magnetic layer 11b may be a reference layer. One of the second magnetic layer 12a and the second opposing magnetic layer 12b may be a magnetization free layer. The other of the second magnetic layer 12a and the second opposing magnetic layer 12b may be a reference layer. One of the third magnetic layer 13a and the third opposing magnetic layer 13b may be a magnetization free layer. The other of the third magnetic layer 13a and the third opposing magnetic layer 13b may be a reference layer. One of the fourth magnetic layer 14a and the fourth opposing magnetic layer 14b may be a magnetization free layer. The other of the fourth magnetic layer 14a and the fourth opposing magnetic layer 14b may be a reference layer.

As shown in FIG. 2, the element portion 10E may further include a first magnetic member 51 and a first opposing magnetic member 51A. The first magnetic member 51 includes a first magnetic end portion 51e and a first magnetic other end portion 51f. A direction from the first magnetic end portion 51e to the first magnetic other end portion 51f is along the third direction D3.

The first opposing magnetic member 51A includes a first opposing magnetic end portion 51Ae and a first opposing magnetic other end portion 51Af. A direction from the first opposing magnetic end portion 51Ae to the first opposing magnetic other end portion 51Af is along the third direction D3.

A position of at least a part of the first magnetic element 11 in the third direction D3 is between a position of the first magnetic other end portion 51f in the third direction D3 and a position of the first opposing magnetic end portion 51Ae in the third direction D3.

As shown in FIG. 3, the element portion 10E may further include a second magnetic member 52 and a second opposing magnetic member 52A. The second magnetic member 52 includes a second magnetic end portion 52e and a second magnetic other end portion 52f. A direction from the second magnetic end portion 52e to the second magnetic other end portion 52f is along the third direction D3.

The second opposing magnetic member 52A includes a second opposing magnetic end portion 52Ae and a second opposing magnetic other end portion 52Af. A direction from the second opposing magnetic end portion 52Ae to the second opposing magnetic other end portion 52Af is along the third direction D3.

A position of at least a part of the second magnetic element 12 in the third direction D3 is between a position of the second magnetic other end portion 52f in the third direction D3 and a position of the second opposing magnetic end portion 52Ae in the third direction D3.

As shown in FIG. 2, the element portion 10E may further include a third magnetic member 53 and a third opposing magnetic member 53A. The third magnetic member 53 includes a third magnetic end portion 53e and a third magnetic other end portion 53f. A direction from the third magnetic end portion 53e to the third magnetic other end portion 53f is along the third direction D3.

The third opposing magnetic member 53A includes a third opposing magnetic end portion 53Ae and a third opposing magnetic other end portion 53Af. A direction from the third opposing magnetic end portion 53Ae to the third opposing magnetic other end portion 53Af is along the third direction D3.

A position of at least a part of the third magnetic element 13 in the third direction D3 is between a position of the third magnetic other end portion 53f in the third direction D3 and a position of the third opposing magnetic end portion 53Ae in the third direction D3.

As shown in FIG. 3, the element portion 10E may further include a fourth magnetic member 54 and a fourth opposing magnetic member 54A. The fourth magnetic member 54 includes a fourth magnetic end portion 54e and a fourth magnetic other end portion 54f. A direction from the fourth magnetic end portion 54e to the fourth magnetic other end portion 54f is along the third direction D3.

The fourth opposing magnetic member 54A includes a fourth opposing magnetic end portion 54Ae and a fourth opposing magnetic other end portion 54Af. A direction from the fourth opposing magnetic end portion 54Ae to the fourth opposing magnetic other end portion 54Af is along the third direction D3.

A position of at least a part of the fourth magnetic element 14 in the third direction D3 is between a position of the fourth magnetic other end portion 54f in the third direction D3 and a position of the fourth opposing magnetic end portion 54Ae in the third direction D3.

The first magnetic member 51, the first opposing magnetic member 51A, the second magnetic member 52, the second opposing magnetic member 52A, the third magnetic member 53, the third opposing magnetic member 53A, the fourth magnetic member 54 and the fourth opposing magnetic member 54A functions as an MFC (Magnetic Flux Concentrator), for example. The first opposing magnetic member 51A may be continuous with the third magnetic member 53. The boundary between the first opposing magnetic member 51A and the third magnetic member 53 may be unclear or clear. One magnetic member may be used as the first opposing magnetic member 51A and the third magnetic member 53. The second opposing magnetic member 52A may be continuous with the fourth magnetic member 54. The boundary between the second opposing magnetic member 52A and the fourth magnetic member 54 may be unclear or clear. One magnetic member may be used as the second opposing magnetic member 52A and the fourth magnetic member 54.

As shown in FIG. 2, in this example, a position of the first conductive member 21 in the second direction D2 is between a position of the conductive layer 65 in the second direction D2 and a position of the first magnetic element 11 in the second direction D2.

As shown in FIG. 3, in this example, a position of the second conductive member 22 in the second direction D2 is between the position of the conductive layer 65 in the second direction D2 and a position of the second magnetic element 12 in the second direction D2.

As shown in FIG. 2, in this example, a position of the third conductive member 23 in the second direction D2 is between the position of the conductive layer 65 in the second direction D2 and a position of the third magnetic element 13 in the second direction D2.

As shown in FIG. 3, in this example, a position of the fourth conductive member 24 in the second direction D2 is between the position of the conductive layer 65 in the second direction D2 and a position of the fourth magnetic element 14 in the second direction D2.

As shown in FIGS. 2 and 3, the magnetic sensor 110 may further include a first substrate 66a and a first insulating member 67a. The conductive layer 65 is provided between the first substrate 66a and the element portion 10E. The first insulating member 67a is provided between the conductive layer 65 and the element portion 10E. The first substrate 66a is, for example, a mounting board. The first insulating member 67a is, for example, an insulating layer. The first insulating member 67a may include at least one of metal oxide or resin, for example. The conductive layer 65 is protected by the first insulating member 67a.

As shown in FIGS. 2 and 3, the magnetic sensor 110 may further include a second insulating member 67b. The second insulating member 67b is provided between the first insulating member 67a and the element portion 10E. The second insulating member 67b fixes the element portion 10E to the first insulating member 67a. The second insulating member 67b is, for example, an adhesive.

As shown in FIGS. 2 and 3, in the magnetic sensor 110, the element portion 10E may further include a second substrate 66b. A direction from the second substrate 66b to the first magnetic element 11 and a direction from the second substrate 66b to the first conductive member 21 are along the second direction D2. A direction from the second substrate 66b to the second magnetic element 12 and a direction from the second substrate 66b to the second conductive member 22 are along the second direction D2. A direction from the second substrate 66b to the third magnetic element 13 and a direction from the second substrate 66b to the third conductive member 23 are along the second direction D2. A direction from the second substrate 66b to the fourth magnetic element 14 and a direction from the second substrate 66b to the fourth conductive member 24 are along the second direction D2. The second substrate 66b is, for example, a Si substrate. The second substrate 66b is fixed to the first insulating member 67a by the second insulating member 67b.

As shown in FIGS. 2 and 3, the element portion 10E may include an element insulating layer 10i. The element insulating layer 10i is provided around the magnetic element, the conductive member, and the magnetic member.

Several examples of the conductive layer current IL in the first period TP1 will be described below.

FIGS. 6A to 6D are schematic diagrams illustrating the operation of the magnetic sensor according to the first embodiment.

The horizontal axis of these figures is time tm. The vertical axis of these figures is the conductive layer current IL.

Figure 6A:
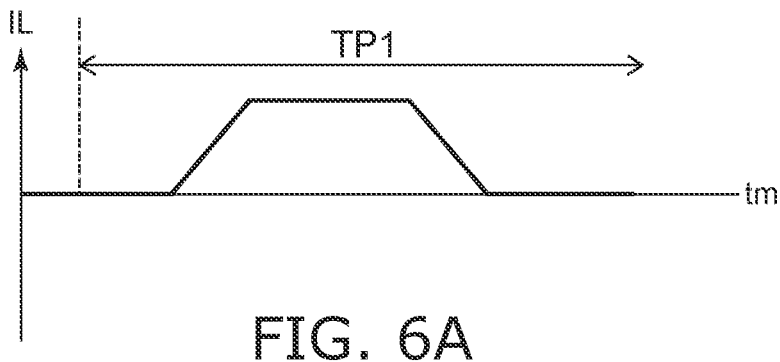
FIGS. 6A to 6D are schematic diagrams illustrating the operation of the magnetic sensor according to the first embodiment.

In one example, the conductive layer current IL may include one pulse (current pulse), as shown in FIG. 6A. The conductive layer current IL may be a DC pulse.

Figure 6B:
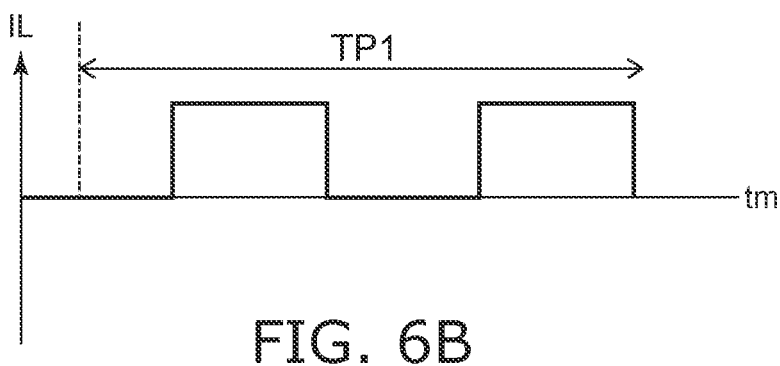

In one example, the conductive layer current IL may include a plurality of pulses (current pulses), as shown in FIG. 6B. The conductive layer current IL may be a plurality of DC pulses.

Figure 6C:
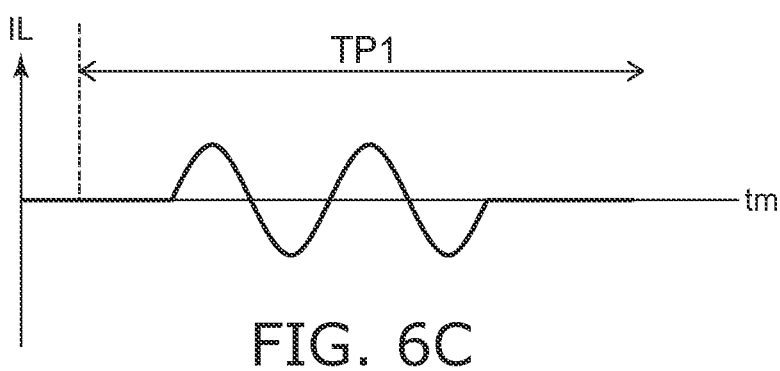

In one example, the conductive layer current IL may include an alternating current, as shown in FIG. 6C. The alternating current may vary non-linearly. The conductive layer current IL may, for example, be sinusoidal. The conductive layer current IL may be triangular, for example.

Figure 6D:
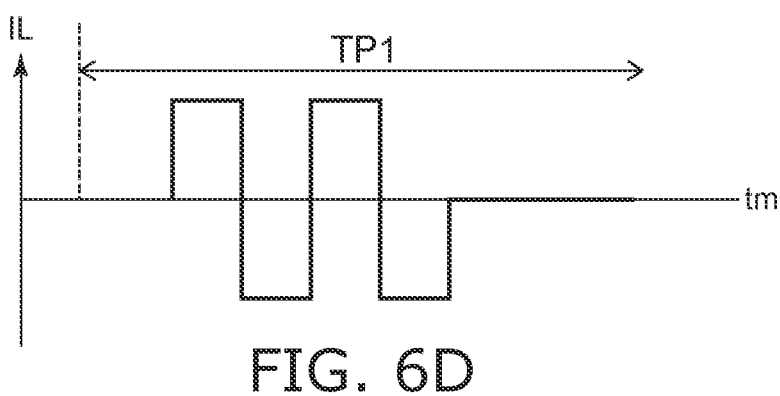

In one example, the conductive layer current IL may be square wave, as shown in FIG. 6D. Thus, in embodiments, the conductive layer current IL may include one or more pulses, direct current, and/or alternating current.

Figure 7A:
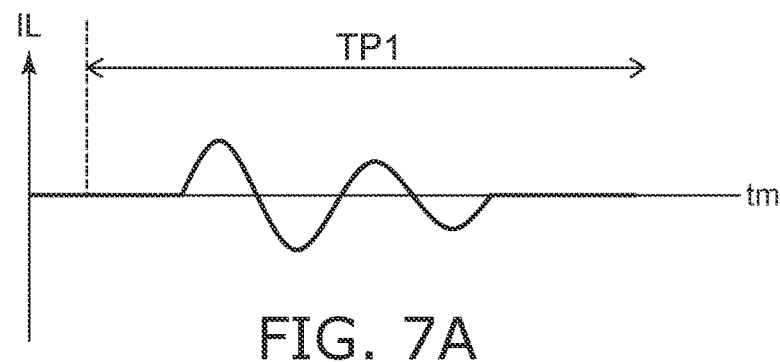
FIGS. 7A and 7B are schematic diagrams illustrating the operation of the magnetic sensor according to the first embodiment.
Figure 7B:
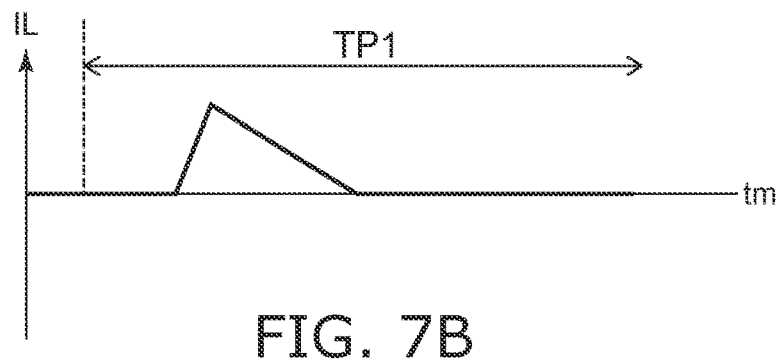

FIGS. 7A and 7B are schematic diagrams illustrating the operation of the magnetic sensor according to the first embodiment.

The horizontal axis of these figures is time tm. The vertical axis of these figures is the conductive layer current IL.

As shown in FIGS. 7A and 7B, the conductive layer current IL may be attenuated with time in the first period TP1. In this case, the conductive layer current IL may an alternating current. The conductive layer current IL may be a direct current.

An example of change in electrical resistance in the magnetic element will be described below.

Figure 8:
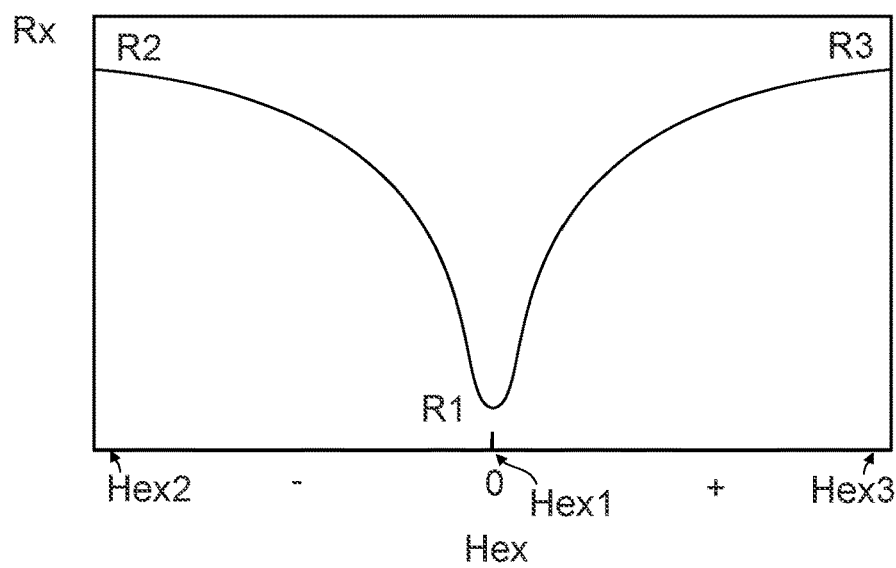
FIG. 8 is a graph diagram illustrating characteristics of the magnetic sensor according to the first embodiment.

FIG. 8 is a graph diagram illustrating characteristics of the magnetic sensor according to the first embodiment.

The horizontal axis of FIG. 8 is the intensity of the external magnetic field Hex applied to the first magnetic element 11. The vertical axis is the electrical resistance Rx of the first magnetic element 11. FIG. 8 corresponds to RH characteristics (resistance-magnetic field characteristics).

As shown in FIG. 8, the electrical resistance Rx has an even function characteristic with respect to the magnetic field applied to the first magnetic element 11 (the external magnetic field Hex, e.g., the magnetic field in the X-axis direction). For example, the electrical resistance Rx has a first value R1 when the first magnetic field Hex1 is applied to the first magnetic element 11. The electrical resistance Rx has a second value R2 when the second magnetic field Hex2 is applied to the first magnetic element 11. The electrical resistance Rx has a third value R3 when the third magnetic field Hex3 is applied to the first magnetic element 11. The absolute value of the first magnetic field Hex1 is smaller than the absolute value of the second magnetic field Hex2 and smaller than the absolute value of the third magnetic field Hex3. For example, the first magnetic field Hex1 is substantially zero. The direction of the second magnetic field Hex2 is opposite to the direction of the third magnetic field Hex3. The first value R1 is less than the second value R2 and less than the third value R3.

An example in which the first current I1 is an alternating current and does not substantially include a direct current component will be described below. The first current I1 (alternating current) is supplied to the first conductive member 21. An alternating magnetic field generated by the alternating current is applied to the first magnetic element 11. An example of change in the electrical resistance Rx at this time will be described.

Figure 9A:
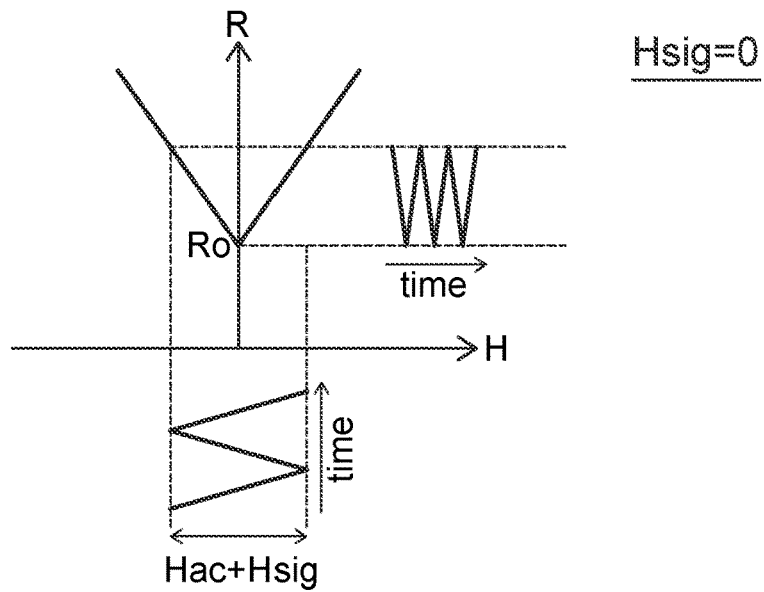
FIGS. 9A to 9C are graphs illustrating characteristics of the magnetic sensor according to the first embodiment.
Figure 9B:
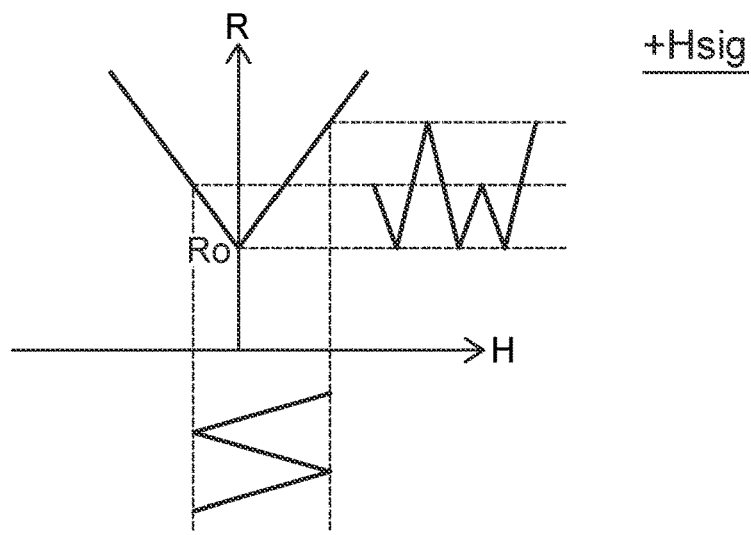
Figure 9C:
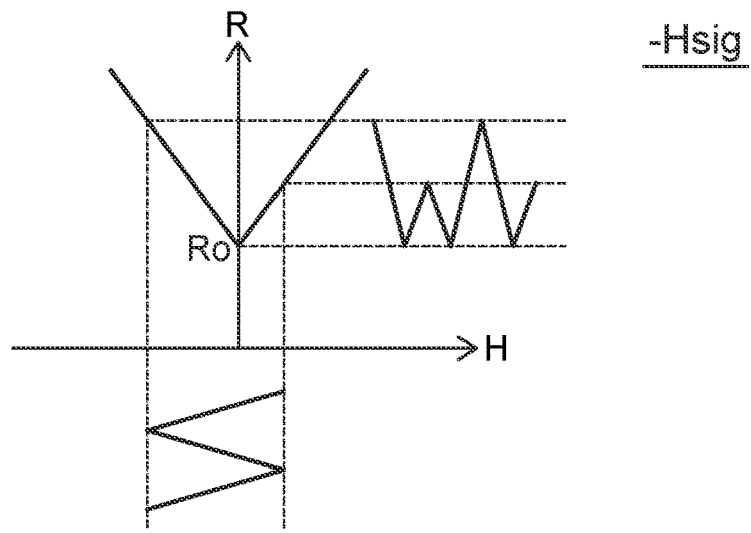

FIGS. 9A to 9C are graphs illustrating characteristics of the magnetic sensor according to the first embodiment.

FIG. 9A shows the characteristics when the signal magnetic field Hsig (external magnetic field) applied to the first magnetic element 11 is zero. FIG. 9B shows the characteristics when the signal magnetic field Hsig is positive. FIG. 9C shows the characteristics when the signal magnetic field Hsig is negative. These figures show the relationship between magnetic field H and resistance R (corresponding to electrical resistance Rx).

As shown in FIG. 9A, when the signal magnetic field Hsig is 0, the resistance R shows symmetrical characteristics with respect to the positive and negative magnetic fields H. When the alternating magnetic field Hac is zero, the resistance R has a low resistance Ro. For example, the magnetization of the magnetization free layer rotates substantially to the same extent for positive and negative magnetic fields H. Therefore, for example, a symmetrical resistance change can be obtained. The change of the resistance R with respect to the alternating magnetic field Hac has the same value for positive and negative polarities. The period of change of the resistance R is half the period of the alternating magnetic field Hac. The change in resistance R has substantially no frequency component of Hac (the alternating magnetic field).

As shown in FIG. 9B, when a positive signal magnetic field Hsig is applied, the change of the resistance R shift to the positive magnetic field H side. The amplitude of the resistance change increases for the positive side of the alternating magnetic field Hac. The amplitude of the resistance change becomes smaller for the negative side of the alternating magnetic field Hac.

As shown in FIG. 9C, when a negative signal magnetic field Hsig is applied, the change of the resistance R shift to the negative magnetic field H side. The amplitude of the resistance change is small for the positive side of Hac. The amplitude of the resistance change increases for the negative side of Hac.

When a non-zero signal magnetic field Hsig is applied, the resistance R changes differently depending on whether the alternating magnetic field Hac is in the positive side or the negative side. The period of change of the resistance R by the alternating magnetic field Hac is ½ of the period of the alternating magnetic field Hac. On the other hand, the period of change of the resistance R by the signal magnetic field Hsig is the same as that of the alternating magnetic field Hac.

The above characteristics are for the case when the signal magnetic field Hsig does not change with time. When the signal magnetic field Hsig changes with time, it becomes as follows. The frequency of the signal magnetic field Hsig is defined as a signal frequency fsig. The frequency of the alternating magnetic field Hac is defined as an alternating frequency fac. In this case, an output signal corresponding to the signal magnetic field Hsig is observed at frequencies of fac±fsig.

When the signal magnetic field Hsig changes with time, the signal frequency fsig is, for example, 1 kHz or less. On the other hand, the alternating frequency fac is sufficiently higher than the signal frequency fsig. For example, the alternating frequency fac is ten times larger or more than the signal frequency fsig.

For example, the signal magnetic field Hsig can be detected with high accuracy by detecting the output voltage with the component of the same period (frequency) as the period (frequency) of the alternating magnetic field Hac. In the magnetic sensor 110 according to the embodiment, by using such method, the external magnetic field Hex (signal magnetic field Hsig) can be detected with high sensitivity. In the embodiment, the external magnetic field Hex (signal magnetic field Hsig) and the alternating magnetic field Hac by the first current I1 can be efficiently applied to the first magnetic element 11. High sensitivity is obtained.

Figure 10A:
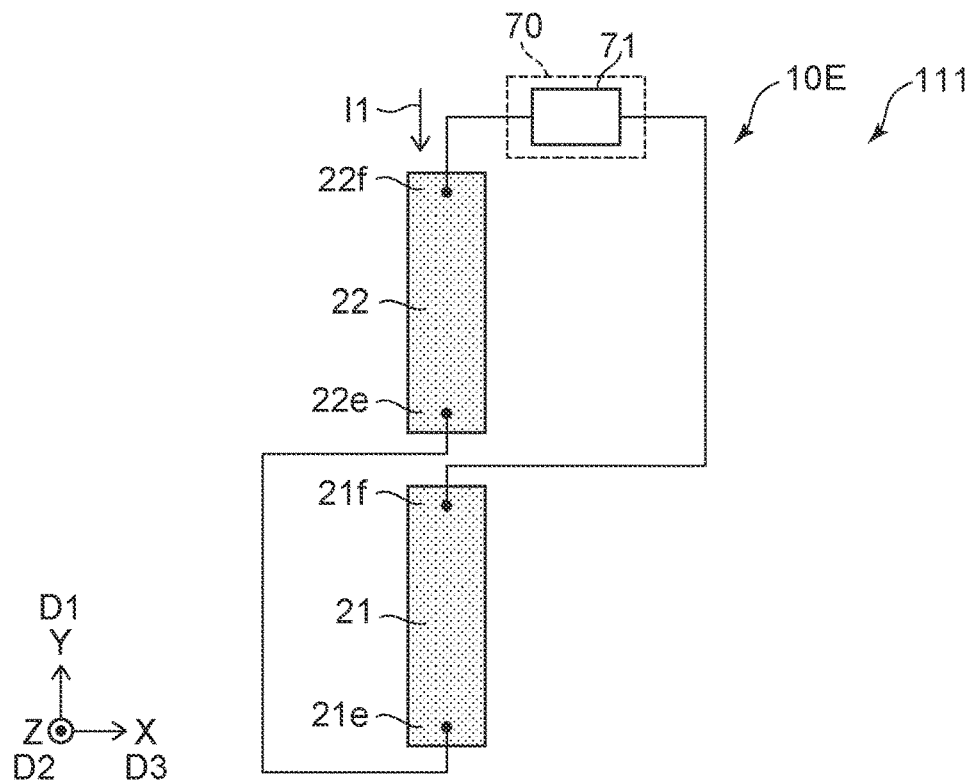
FIGS. 10A and 10B are schematic plan views illustrating the magnetic sensor according to the first embodiment.
Figure 10B:
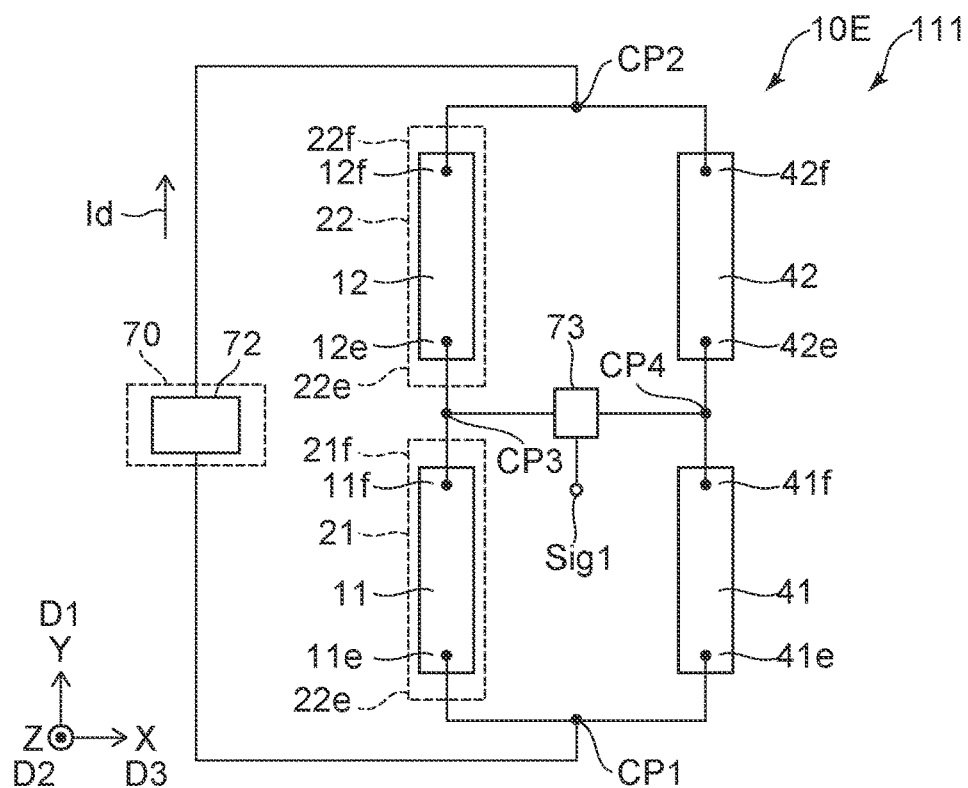

FIGS. 10A and 10B are schematic plan views illustrating the magnetic sensor according to the first embodiment.

These figures illustrate a magnetic sensor 111 according to the embodiment. In the magnetic sensor 111, the first resistance element 41 and the second resistance element 42 are provided, and the third conductive member 23 and the fourth conductive member 24 are omitted. Except for this, the configuration of the magnetic sensor 111 may be the same as the configuration of the magnetic sensor 110, for example.

As shown in FIG. 10B, the element portion 10E further includes a first resistance element 41 and a second resistance element 42.

The first resistance element 41 includes a first resistance end portion 41e and a first resistance other end portion 41f. In this example, a direction from the first resistance end portion 41e to the first resistance other end portion 41f is along the first direction D1. The first resistance end portion 41e is electrically connected to the first end portion 11e. The second resistance element 42 includes a second resistance end portion 42e and a second resistance other end portion 42f. In this example, the direction from the second resistance end portion 42e to the second resistance other end portion 42f is along the first direction D1. The second resistance end portion 42e is electrically connected to the first resistance other end portion 41f. The second resistance other end portion 42f is electrically connected to the second other end portion 12f.

In the detection operation OP1, the second circuit 72 supplies the element current Id (or element voltage) between the first connection point CP1 of the first end portion 11e and the first resistance end portion 41e, and the second connection point CP2 of the second other end portion 12f and the second resistance other end portion 42f. The element current Id flows through the first resistance element 41 and the second resistance element 42. In this example, the element current Id flows from the first resistance other end portion 41f to the first resistance end portion 41e. The element current Id flows from the second resistance other end portion 42f to the second resistance end portion 42e.

In the detection operation OP1, the third circuit 73 is configured to detect the detection signal Sig1 corresponding to the potential difference between the third connection point CP3 of the first other end portion 11f and the second end portion 12e, and the fourth connection point CP4 of the first resistance other end portion 41f and the second resistance end portion 42e.

As described above, the first current I1 flows through the first conductive member 21 and the second conductive member 22 (see FIG. 10A). In the magnetic sensor 111, the bridge circuit (so-called half bridge circuit) including the first magnetic element 11, the second magnetic element 12, the first resistance element 41, and the second resistance element 42 is used. Highly accurate detection with reduced noise is possible.

The configuration of the first resistance element 41 and the configuration of the second resistance element 42 are arbitrary. For example, the configuration of at least a part of the third magnetic element 13 may be applied to the first resistance element 41. For example, the configuration of at least a part of the fourth magnetic element 14 may be applied to the second resistance element 42.

Figure 11A:
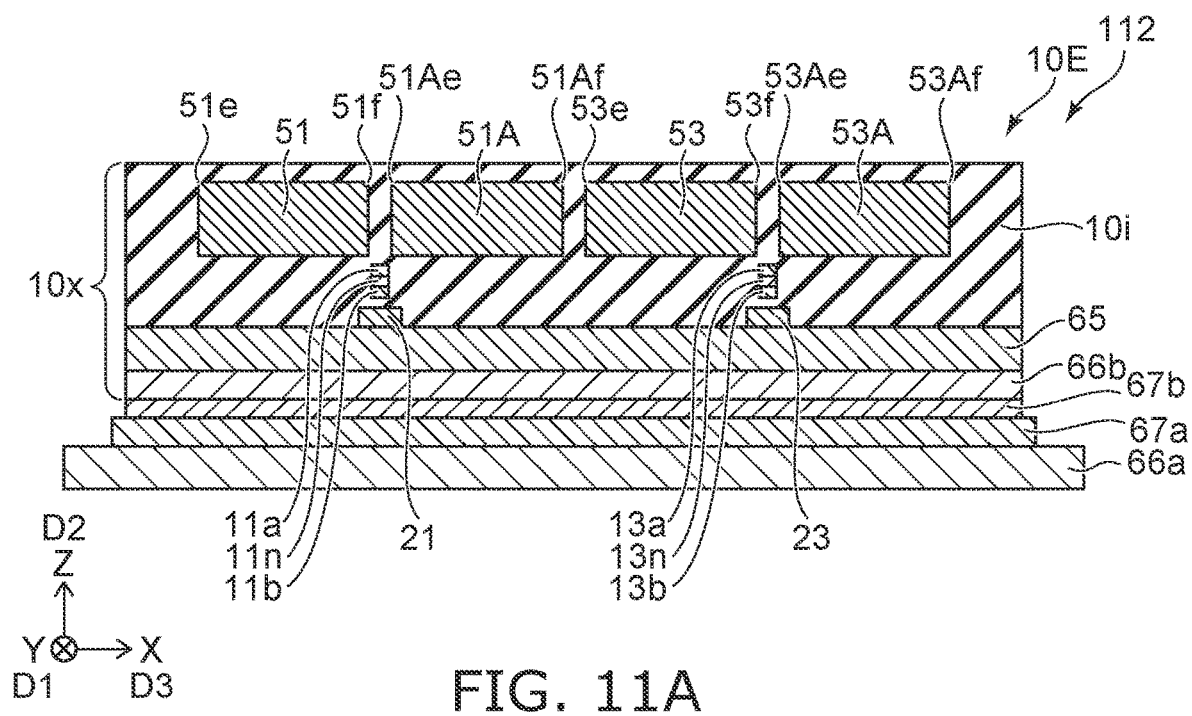
FIGS. 11A and 11B are schematic cross-sectional views illustrating the magnetic sensor according to the first embodiment.
Figure 11B:
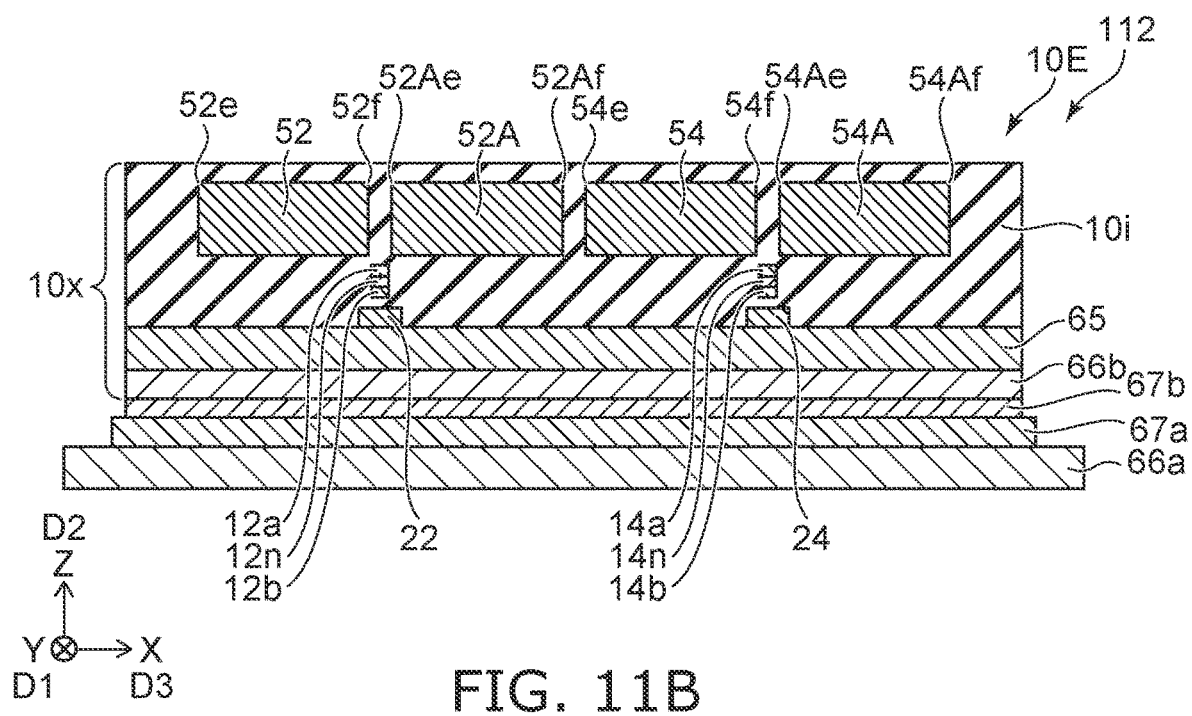

FIGS. 11A and 11B are schematic cross-sectional views illustrating the magnetic sensor according to the first embodiment.

These figures illustrate a magnetic sensor 112 according to the embodiment. In magnetic sensor 112, the position of conductive layer 65 is different from the position of conductive layer 65 in magnetic sensor 110. Except for this, the configuration of the magnetic sensor 112 may be the same as the configuration of the magnetic sensor 110 or the magnetic sensor 111.

The magnetic sensor 112 includes the first substrate 66a, the second substrate 66b, and the first insulating member 67a. The first insulating member 67a is provided between the first substrate 66a and the structural body 10x.

The structural body 10x includes the element portion 10E, the conductive layer 65, and the second substrate 66b. The conductive layer 65 is provided between the second substrate 66b and the element portion 10E. The structural body 10x is a sensor chip including the element portion 10E and the conductive layer 65. The conductive layer 65 is provided in the sensor chip.

In the magnetic sensor 112, the second insulating member 67b may be provided. The second insulating member 67b is provided between the first insulating member 67a and the second substrate 66b.

An example of the circuit portion 70 will be described below.

Figure 12:
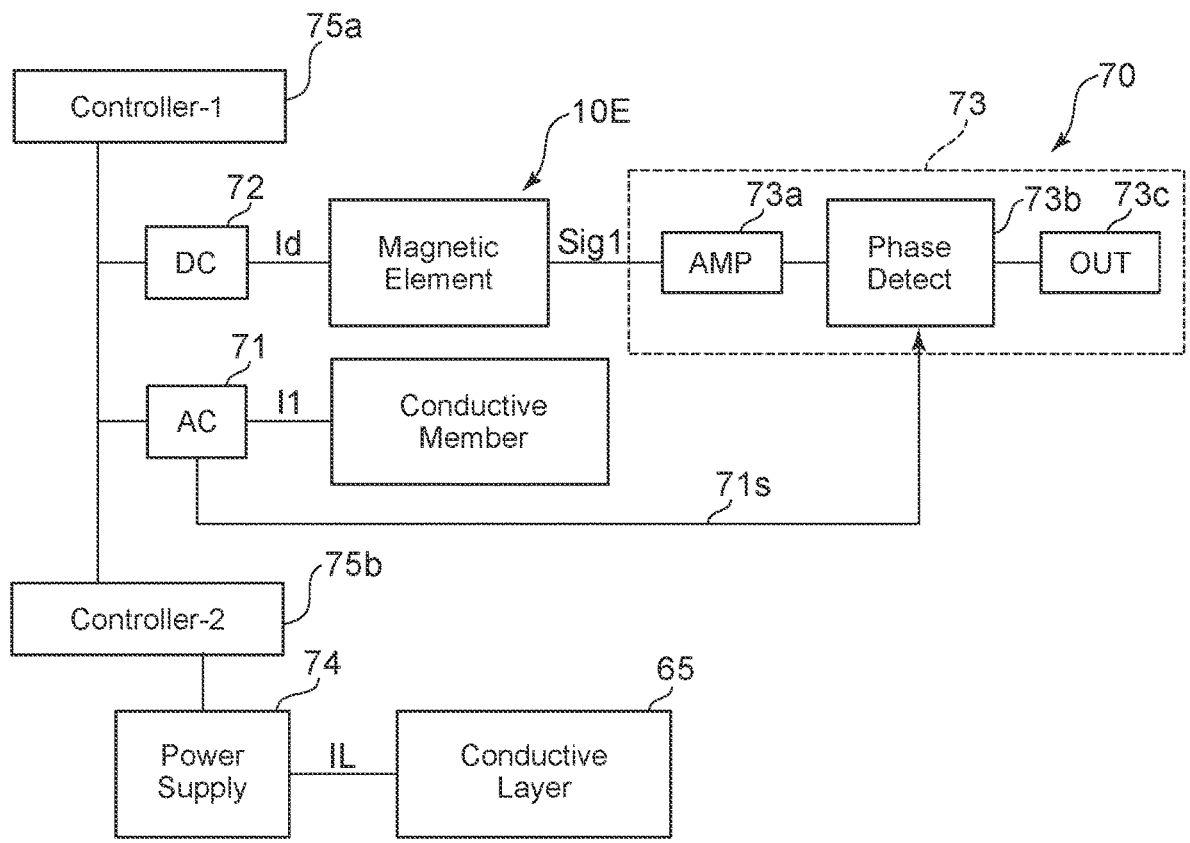
FIG. 12 is a schematic diagram illustrating the magnetic sensor according to the first embodiment.

FIG. 12 is a schematic diagram illustrating the magnetic sensor according to the first embodiment.

As shown in FIG. 12, the circuit portion 70 includes the first circuit 71, the second circuit 72, the third circuit 73 and a current circuit 74. The circuit portion 70 may include a first controller 75a and a second controller 75b.

The first controller 75a is configured to control the entire circuit. For example, the first controller 75a sets the first period TP1 and the second period TP2.

The second controller 75b is controlled by the first controller 75a. The second controller 75b is configured to control the current circuit 74 (power source). The conductive layer current IL is supplied from the current circuit 74 to the conductive layer 65 in the first period TP1. The conductive layer current IL is not supplied to the conductive layer 65 in the second period TP2.

For example, the first circuit 71 and the second circuit 72 are controlled by the first controller 75a. For example, in the second period TP2, the first current I1 is supplied from the first circuit 71 to the conductive member (element portion 10E). For example, in the second period TP2, the element current Id is supplied from the second circuit 72 to the magnetic device (the device portion 10E).

The third circuit 73 includes, for example, an amplifier circuit 73a, a phase detection circuit 73b and an output circuit 73c. The amplifier circuit 73a, for example, amplifies the detection signal Sig1 obtained from the bridge circuit. The phase detection circuit 73b detects the output from the amplifier circuit 73a using the AC component of the first current I1 as a reference signal 71s. A reference signal 71s is obtained from the first circuit 71. The output circuit 73c is configured to output the signal obtained from the phase detection circuit 73b to the outside.

Thus, the third circuit 73 is configured to detect the detection signal Sig1 using the AC component included in the first current I1 as the reference signal 71s. Highly accurate detection with suppressed noise becomes possible.

Second Embodiment

The second embodiment relates to an inspection device. As will be described later, the inspection device may include a diagnostic device.

Figure 13:
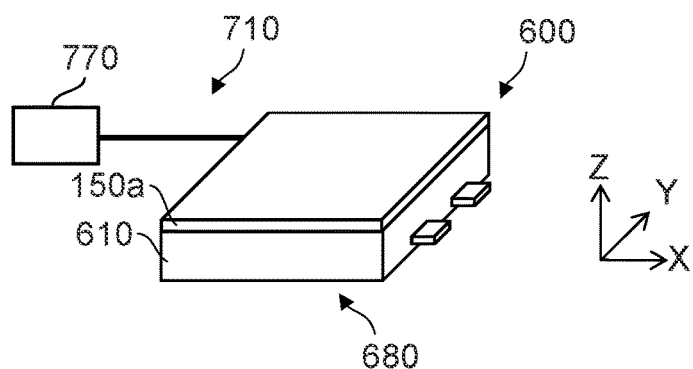
FIG. 13 is a schematic perspective view illustrating an inspection device according to a second embodiment.

FIG. 13 is a schematic perspective view illustrating an inspection device according to a second embodiment.

As shown in FIG. 13, an inspection device 710 according to the embodiment includes a sensor 150a (magnetic sensor) and a processor 770. The sensor 150a may be the sensor according to the first embodiment and a modification thereof. The processor 770 processes an output signal obtained from the sensor 150a. The processor 770 may compare the signal obtained from the sensor 150a with the reference value. The processor 770 can output the inspection result based on the processing result.

For example, the inspection device 710 inspects an inspection object 680. The inspection object 680 is, for example, an electronic device (including a semiconductor circuit or the like). The inspection object 680 may be, for example, a battery 610 or the like.

For example, the sensor 150a according to the embodiment may be used together with the battery 610. For example, a battery system 600 includes the battery 610 and the sensor 150a. The sensor 150a can detect the magnetic field generated by the current flowing through the battery 610.

Figure 14:
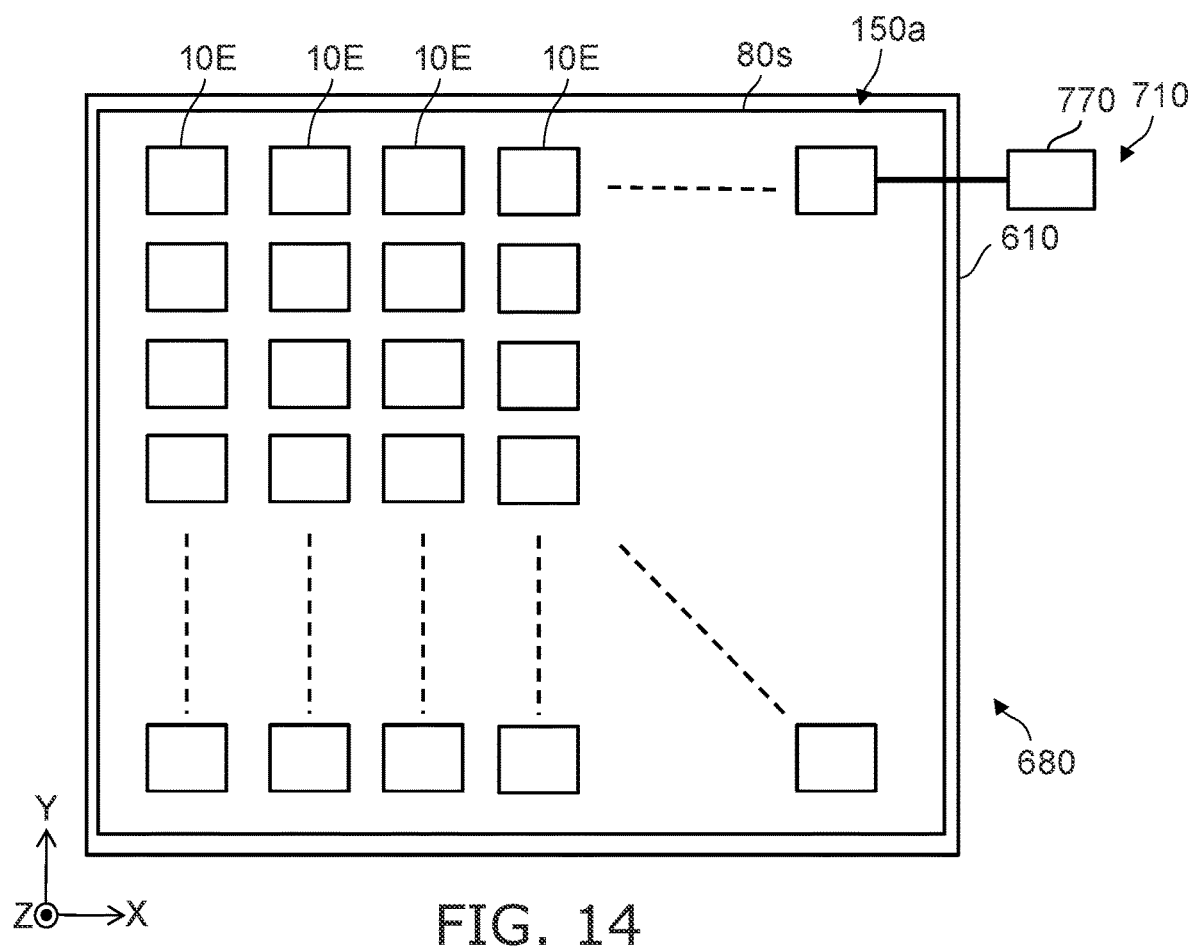
FIG. 14 is a schematic plan view illustrating the inspection device according to the second embodiment.

FIG. 14 is a schematic plan view illustrating the inspection device according to the second embodiment.

As shown in FIG. 14, the sensor 150a includes, for example, multiple sensors according to the embodiment. In this example, the sensor 150a includes multiple sensors (the element portion 10U such as the magnetic sensor 110, etc.). The multiple sensors are arranged along, for example, two directions (for example, the X-axis direction and the Y-axis direction). The multiple magnetic sensors 110 are provided, for example, on a substrate.

The sensor 150a can detect the magnetic field generated by the current flowing through the inspection object 680 (for example, the battery 610 may be used). For example, when the battery 610 approaches an abnormal state, an abnormal current may start to flow through the battery 610. By detecting the abnormal current with the sensor 150a, it is possible to know the change in the state of the battery 610. For example, in a state where the sensor 150a is placed close to the battery 610, the entire battery 610 can be inspected in a short time by moving the sensor array in two directions. The sensor 150a may be used for inspection of the battery 610 in manufacturing process of the battery 610.

The sensor according to the embodiment can be applied to, for example, the inspection device 710 such as a diagnostic device.

Figure 15:
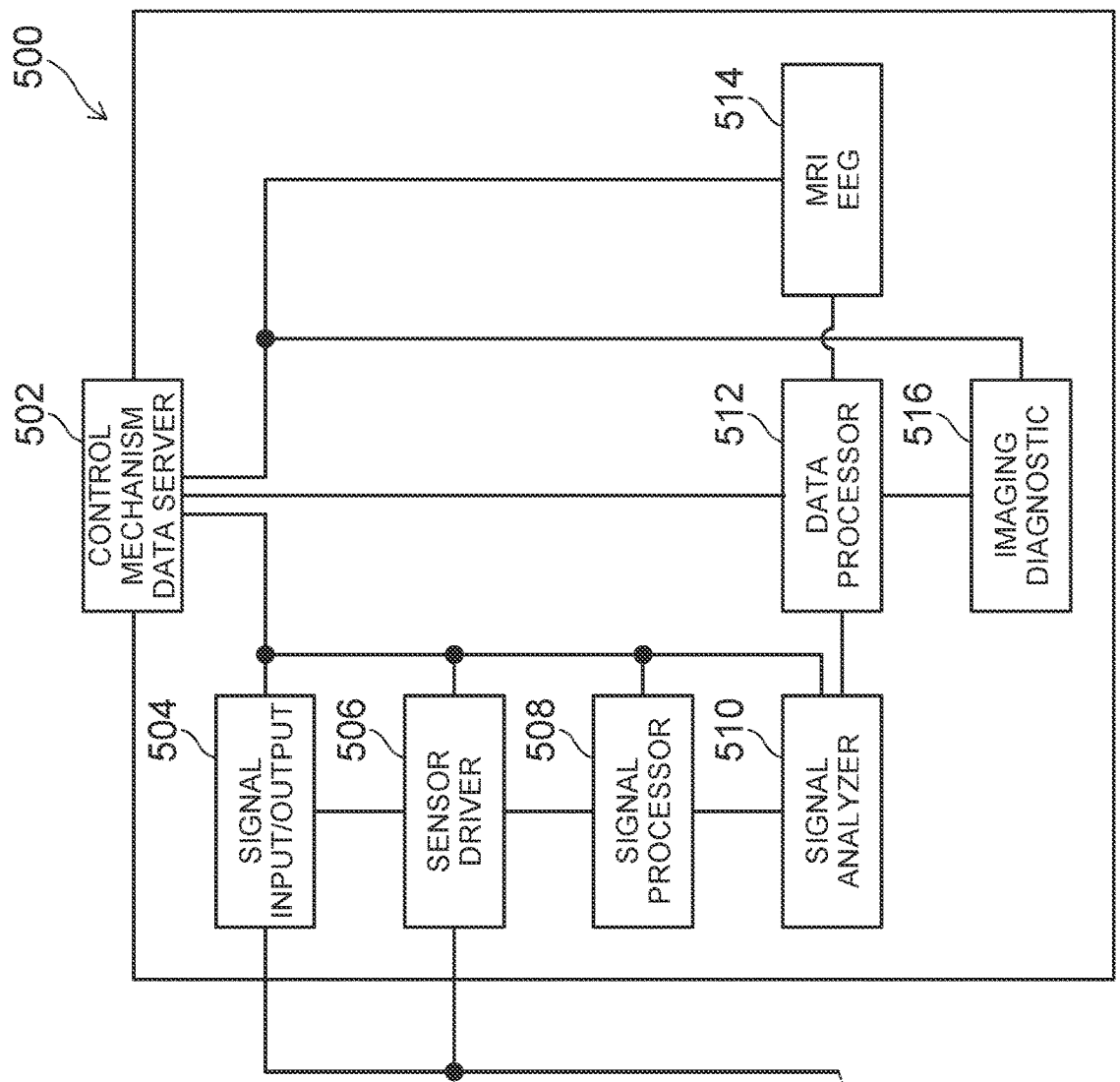
FIG. 15 is a schematic diagram illustrating the sensor and the inspection device according to the embodiment.

FIG. 15 is a schematic diagram illustrating the sensor and the inspection device according to the embodiment.

As shown in FIG. 15, a diagnostic apparatus 500, which is an example of the inspection device 710, includes a sensor 150. The sensor 150 includes the sensors described with respect to the first embodiment and modifications thereof.

In the diagnostic apparatus 500, the sensor 150 is, for example, a magnetoencephalograph. The magnetoencephalograph detects the magnetic field generated by the cranial nerves. When the sensor 150 is used in a magnetoencephalograph, the size of the magnetic element included in the sensor 150 is, for example, not less than 1 mm and less than 10 mm. This size is, for example, the length including an MFC.

As shown in FIG. 15, the sensor 150 (magnetoencephalogram) is attached to, for example, the head of a human body. The sensor 150 (magnetoencephalogram) includes a sensor part 301. The sensor 150 (magnetoencephalogram) may include multiple sensor parts 301. The number of the multiple sensor parts 301 is, for example, about 100 (for example, not less than 50 and not more than 150). The multiple sensor parts 301 are provided on a flexible base body 302.

The sensor 150 may include, for example, a circuit such as differential detection. The sensor 150 may include a sensor other than the sensor (for example, a potential terminal or an acceleration sensor).

A size of the sensor 150 is smaller than a size of a conventional SQUID sensor. Therefore, it is easy to install the multiple sensor parts 301. Installation of the multiple sensor parts 301 and other circuits is easy. The coexistence of the multiple sensor parts 301 and other sensors is easy.

The base body 302 may include an elastic body such as a silicone resin. For example, the multiple sensor parts 301 are provided to be connected to the base body 302. The base body 302 can be in close contact with the head, for example.

The input/output code 303 of the sensor part 301 is connected to a sensor driver 506 and a signal input/output 504 of the diagnostic apparatus 500. The magnetic field measurement is performed in the sensor part 301 based on the electric power from the sensor driver 506 and the control signal from the signal input/output 504. The result is input to the signal input/output 504. The signal obtained by the signal input/output 504 is supplied to a signal processor 508. The signal processor 508 performs processing such as noise removal, filtering, amplification, and signal calculation. The signal processed by the signal processor 508 is supplied to a signal analyzer 510. The signal analyzer 510 extracts, for example, a specific signal for magnetoencephalography measurement. In the signal analyzer 510, for example, signal analysis for matching signal phases is performed.

The output of the signal analyzer 510 (data for which signal analysis has been completed) is supplied to a data processor 512. The data processor 512 performs data analysis. In this data analysis, for example, image data such as MRI (Magnetic Resonance Imaging) can be incorporated. In this data analysis, for example, scalp potential information such as EEG (Electroencephalogram) can be incorporated. For example, a data part 514 such as MRI or EEG is connected to the data processor 512. By the data analysis, for example, nerve ignition point analysis, inverse problem analysis, and the like are performed.

The result of the data analysis is supplied to, for example, an imaging diagnostic 516. Imaging is performed in the imaging diagnostic 516. Imaging assists in diagnosis.

The above series of operations is controlled by, for example, a control mechanism 502. For example, necessary data such as primary signal data or metadata in the middle of data processing is stored in the data server. The data server and the control mechanism may be integrated.

The diagnostic apparatus 500 according to the embodiment includes the sensor 150 and the processor that processes an output signal obtained from the sensor 150. This processor includes, for example, at least one of a signal processor 508 or a data processor 512. The processor includes, for example, a computer.

In the sensor 150 shown in FIG. 15, the sensor part 301 is installed on the head of the human body. The sensor part 301 may be installed on the chest of the human body. This enables magnetocardiography measurement. For example, the sensor part 301 may be installed on the abdomen of a pregnant woman. This makes it possible to perform a fetal heartbeat test.

The sensor device including the subject is preferably installed in a shield room. Thereby, for example, the influence of geomagnetism or magnetic noise can be suppressed.

For example, a mechanism for locally shielding the measurement site of the human body or the sensor part 301 may be provided. For example, the sensor part 301 may be provided with a shield mechanism. For example, effective shielding may be performed in the signal analysis or the data processing.

In embodiments, the base body 302 may be flexible and may be substantially non-flexible. In the example shown in FIG. 15, the base body 302 is a continuous film processed into a hat shape. The base body 302 may be in a net shape. Thereby, for example, good wearability can be obtained. For example, the adhesion of the base body 302 to the human body is improved. The base body 302 may be helmet-shaped and may be rigid.

Figure 16:
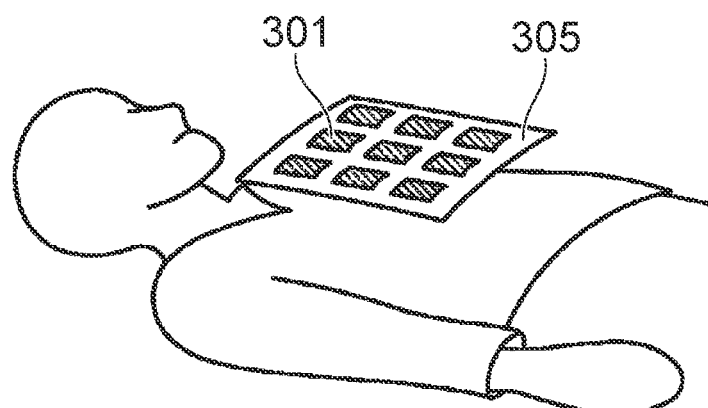
FIG. 16 is a schematic view illustrating the inspection device according to the embodiment.

FIG. 16 is a schematic view illustrating the inspection device according to the embodiment.

In the example shown in FIG. 16, the sensor part 301 is provided on a flat plate-shaped hard base body 305.

In the example shown in FIG. 16, the input/output of the signal obtained from the sensor part 301 is the same as the input/output described with respect to FIG. 15. In the example shown in FIG. 16, the processing of the signal obtained from the sensor part 301 is the same as the processing described with respect to FIG. 15.

There is a reference example of using a SQUID (Superconducting Quantum Interference Device) sensor as a device for measuring a weak magnetic field such as a magnetic field generated from a living body. In this reference example, since superconductivity is used, the device is large and the power consumption is also large. The burden on the measurement target (patient) is heavy.

According to the embodiment, the device can be downsized. Power consumption can be suppressed. The burden on the measurement object (patient) can be reduced. According to the embodiment, the SN ratio of magnetic field detection can be improved. Sensitivity can be improved.

The embodiments may include the following configurations (for example, technical proposals).

Configuration 1

A magnetic sensor, comprising:
an element portion including a first magnetic element, a second magnetic element, a first conductive member, and a second conductive member,
the first magnetic element including a first end portion and a first other end portion, a direction from the first end portion to the first other end portion being along a first direction,
the second magnetic element including a second end portion and a second other end portion, a direction from the second end portion to the second other end portion being along the first direction, the second end portion being electrically connected to the first other end portion,
the first conductive member including a first portion and a first other portion, the first portion corresponding to the first end portion, the first other portion corresponding to the first other end portion, and
the second conductive member including a second portion and a second other portion, the second portion corresponding to the second end portion, the second other portion corresponding to the second other end portion; and
a conductive layer, a second direction from the conductive layer to the element portion crossing the first direction, the conductive layer including a first conductive portion and a first other conductive portion, a third direction from the first conductive portion to the first other conductive portion crossing a plane including the first direction and the second direction.

Configuration 2

The sensor according to Configuration 1, further comprising:
a current circuit; and
a first circuit,
the current circuit being configured to supply a conductive layer current between the first conductive portion and the first other conductive portion in a first period,
the current circuit being configured to not supply the conductive layer current between the first conductive portion and the first other conductive portion in the second period, and
the first circuit being configured to supply a first current including an AC component to the first conductive member and the second conductive member in the second period.

Configuration 3
The sensor according to Configuration 2, wherein the first circuit is configured not to supply the first current to the first conductive member and the second conductive member in the first period.

Configuration 4
The sensor according to Configuration 3, further comprising
a second circuit; and
a third circuit,
the second circuit and the third circuit being configured to perform a detection operation in the second period, and
in the detection operation, the second circuit being configured to supply an element current or an element voltage to the first magnetic element and the second magnetic element, the third circuit being configured to detect a signal corresponding to a difference between a first electrical resistance of the first magnetic element and a second electrical resistance of the second magnetic element.

Configuration 5
The sensor according to Configuration 4, wherein the second circuit and the third circuit are configured to not perform the detection operation in the first period.

Configuration 6
The sensor according to Configuration 4, wherein
the element current flows from the first other end portion to the first end portion,
the element current flows from the second other end portion to the second end portion, and
the first current flows from the first portion to the first other portion when the first current is flowing from the second other portion to the second portion.

Configuration 7
The sensor according to Configuration 6, wherein
the element unit further includes a third magnetic element, a fourth magnetic element, a third conductive member, and a fourth conductive member,
the third magnetic element includes a third end portion and a third other end portion, a direction from the third end portion to the third other end portion is along the first direction, the third end portion is electrically connected to the first end portion,
the fourth magnetic element includes a fourth end portion and a fourth other end portion, a direction from the fourth end portion to the fourth other end portion is along the first direction, the fourth end portion is electrically connected to the third other end portion, the fourth other end portion is electrically connected to the second other end portion,
the third conductive member includes a third portion and a third other portion, the third portion corresponds to the third end portion, the third other portion corresponds to the third other end portion,
the fourth conductive member includes a fourth portion and a fourth other portion, the fourth portion corresponds to the fourth end portion, the fourth other portion corresponds to the fourth other end portion,
the first circuit is configured to supply the first current to the third conductive member and the fourth conductive member in the second period,
in the detection operation, the second circuit is configured to supply the element current or the device voltage to a first connection point of the first end portion and the third end portion, and a second connection point of the second other end portion and the fourth other end portion,
the element current flows from the third other end portion to the third end portion, and
the element current flows from the fourth other end portion to the fourth end portion.

Configuration 8
The sensor according to Configuration 7, wherein in the detection operation, the third circuit is configured to detect a detection signal corresponding to a potential difference between a third connection point of the first other end portion and the second end portion, and a fourth connection point of the third other end portion and the fourth end portion.

Configuration 9
The sensor according to Configuration 8, wherein the third circuit is configured to detect the detection signal using the AC component as a reference signal.

Configuration 10
The sensor according to Configuration 6, wherein
the element portion further includes a first resistance element and a second resistance element,
the first resistance element includes a first resistance end portion and a first resistance other end portion, the first resistance end portion is electrically connected to the first end portion,
the second resistance element includes a second resistance end portion and a second resistance other end portion, the second resistance end portion is electrically connected to the first resistance other end portion, the second resistance other end portion is electrically connected to the second other end portion,
in the detection operation, the second circuit is configured to supply the element current or the device voltage between a first connection point of the first end portion and the first resistance end portion, and a second connection of the second other end portion and the second resistance other end portion,
the element current flows from the first resistance other end portion to the first resistance end portion, and
the element current flows from the second resistance other end portion to the second resistance end portion.

Configuration 11
The sensor according to Configuration 10, wherein in the detection operation, the third circuit is configured to detect a detection signal corresponding to a potential difference between a third connection point of the first other end portion and the second end portion, and a fourth connection point of the first resistance other end portion and the second resistance end portion.

Configuration 12
The sensor according to Configuration 1, further comprising:
a first substrate; and
a first insulating member,
the conductive layer being provided between the first substrate and the element portion, and
the first insulating member is provided between the conductive layer and the element portion.

Configuration 13
The sensor according to Configuration 12, further comprising a second insulating member,
the second insulating member being provided between the first insulating member and the element portion, and
the second insulating member fixing the element portion to the first insulating member.

Configuration 14
The sensor according to Configuration 13, wherein the element portion further includes a second substrate, the second insulating member is provided between the first insulating member and the element portion, and the second insulating member fixes the element portion to the first insulating member.

Configuration 15
The sensor according to Configuration 1, further comprising:
a first substrate;
a second substrate; and
a first insulating member,
the first insulating member being provided between the first substrate and a structure,
the structure including the element portion, the conductive layer, and the second substrate, and
the conductive layer being provided between the second substrate and the element portion.

Configuration 16
The sensor according to any one of Configurations 2 to 6, wherein the conductive layer current includes at least one of one or more pulses, a direct current, and an alternating current.

Configuration 17
The sensor according to any one of Configurations 2 to 6, wherein the conductive layer current is attenuated with lapse of time in the first period.

Configuration 18
The sensor according to any one of Configurations 1 to 17, wherein
the element portion further includes a first magnetic member and a first opposing magnetic member,
the first magnetic member includes a first magnetic end portion and a first magnetic other end portion, a direction from the first magnetic end portion to the first magnetic other end portion is along the third direction,
the first opposing magnetic member includes a first opposing magnetic end portion and a first opposing magnetic other end portion, a direction from the first opposing magnetic end portion to the first opposing magnetic other end portion is along the third direction, and
a position of at least a part of the first magnetic element in the third direction is between a position of the first magnetic other end portion in the third direction and a position of the first opposing magnetic end portion in the third direction.

Configuration 19
The sensor according to any one of Configurations 1 to 18, wherein a position of the first conductive member in the second direction is between a position of the conductive layer in the second direction and a position of the first magnetic element in the second direction.

Configuration 20
An inspection device, comprising:
the magnetic sensor according to any one of Configurations 1 to 19; and
a processor configured to process an output signal obtained from the magnetic sensor.

According to the embodiments, it is possible to provide a magnetic sensor and an inspection device capable of improving sensitivity.

In the present specification, "perpendicular" and "parallel" include not only strict perpendicularity and strict parallelism, but also variations in the manufacturing process, for example, and may be substantially perpendicular and substantially parallel.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in the magnetic sensors such as element portions, magnetic elements, magnetic layers, non-magnetic layers, conductive members, conductive layers circuit, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all magnetic sensors and all inspection devices practicable by an appropriate design modification by one skilled in the art based on the magnetic sensors and the inspection devices described above as embodiments of the invention also are within the scope of the invention to the extent that the purport of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:
1. A magnetic sensor, comprising:
an element portion including a first magnetic element, a second magnetic element, a first conductive member, and a second conductive member,
the first magnetic element including a first end portion and a first other end portion, a direction from the first end portion to the first other end portion being along a first direction,
the second magnetic element including a second end portion and a second other end portion, a direction from the second end portion to the second other end portion being along the first direction, the second end portion being electrically connected to the first other end portion,
the first conductive member including a first portion and a first other portion, the first portion corresponding to the first end portion, the first other portion corresponding to the first other end portion, and
the second conductive member including a second portion and a second other portion, the second portion corresponding to the second end portion, the second other portion corresponding to the second other end portion;
a conductive layer, a second direction from the conductive layer to the element portion crossing the first direction, the conductive layer including a first conductive por- tion and a first other conductive portion, a third direction from the first conductive portion to the first other conductive portion crossing a plane including the first direction and the second direction;
a current circuit; and
a first circuit,
the current circuit being configured to supply a conductive layer current between the first conductive portion and the first other conductive portion in a first period,
the current circuit being configured to not supply the conductive layer current between the first conductive portion and the first other conductive portion in a second period, and
the first circuit being configured to supply a first current including an AC component to the first conductive member and the second conductive member in the second period.

2. The sensor according to claim 1, wherein the first circuit is configured not to supply the first current to the first conductive member and the second conductive member in the first period.

3. The sensor according to claim 2, further comprising
a second circuit; and
a third circuit,
the second circuit and the third circuit being configured to perform a detection operation in the second period, and
in the detection operation, the second circuit being configured to supply an element current or an element voltage to the first magnetic element and the second magnetic element, the third circuit being configured to detect a signal corresponding to a difference between a first electrical resistance of the first magnetic element and a second electrical resistance of the second magnetic element.

4. The sensor according to claim 3, wherein the second circuit and the third circuit are configured to not perform the detection operation in the first period.

5. The sensor according to claim 3, wherein
the element current flows from the first other end portion to the first end portion,
the element current flows from the second other end portion to the second end portion, and
the first current flows from the first portion to the first other portion when the first current is flowing from the second other portion to the second portion.

6. The sensor according to claim 5, wherein
the element portion further includes a third magnetic element, a fourth magnetic element, a third conductive member, and a fourth conductive member,
the third magnetic element includes a third end portion and a third other end portion, a direction from the third end portion to the third other end portion is along the first direction, the third end portion is electrically connected to the first end portion,
the fourth magnetic element includes a fourth end portion and a fourth other end portion, a direction from the fourth end portion to the fourth other end portion is along the first direction, the fourth end portion is electrically connected to the third other end portion, the fourth other end portion is electrically connected to the second other end portion,
the third conductive member includes a third portion and a third other portion, the third portion corresponds to the third end portion, the third other portion corresponds to the third other end portion,
the fourth conductive member includes a fourth portion and a fourth other portion, the fourth portion corresponds to the fourth end portion, the fourth other portion corresponds to the fourth other end portion,
the first circuit is configured to supply the first current to the third conductive member and the fourth conductive member in the second period,
in the detection operation, the second circuit is configured to supply the element current or a device voltage to a first connection point of the first end portion and the third end portion, and a second connection point of the second other end portion and the fourth other end portion,
the element current flows from the third other end portion to the third end portion, and
the element current flows from the fourth other end portion to the fourth end portion.

7. The sensor according to claim 6, wherein in the detection operation, the third circuit is configured to detect a detection signal corresponding to a potential difference between a third connection point of the first other end portion and the second end portion, and a fourth connection point of the third other end portion and the fourth end portion.

8. The sensor according to claim 7, wherein the third circuit is configured to detect the detection signal using the AC component as a reference signal.

9. The sensor according to claim 5, wherein
the element portion further includes a first resistance element and a second resistance element,
the first resistance element includes a first resistance end portion and a first resistance other end portion, the first resistance end portion is electrically connected to the first end portion,
the second resistance element includes a second resistance end portion and a second resistance other end portion, the second resistance end portion is electrically connected to the first resistance other end portion, the second resistance other end portion is electrically connected to the second other end portion,
in the detection operation, the second circuit is configured to supply the element current or a device voltage between a first connection point of the first end portion and the first resistance end portion, and a second connection of the second other end portion and the second resistance other end portion,
the element current flows from the first resistance other end portion to the first resistance end portion, and
the element current flows from the second resistance other end portion to the second resistance end portion.

10. The sensor according to claim 9, wherein in the detection operation, the third circuit is configured to detect a detection signal corresponding to a potential difference between a third connection point of the first other end portion and the second end portion, and a fourth connection point of the first resistance other end portion and the second resistance end portion.

11. The sensor according to claim 1, further comprising:
a first substrate;
a second substrate; and
a first insulating member,
the first insulating member being provided between the first substrate and a structure,
the structure including the element portion, the conductive layer, and the second substrate, and
the conductive layer being provided between the second substrate and the element portion.

12. The sensor according to claim 1, wherein the conductive layer current includes at least one of one or more pulses, a direct current, and an alternating current.

13. The sensor according to claim 1, wherein the conductive layer current is attenuated with lapse of time in the first period.

14. The sensor according to claim 1, wherein
the element portion further includes a first magnetic member and a first opposing magnetic member,
the first magnetic member includes a first magnetic end portion and a first magnetic other end portion, a direction from the first magnetic end portion to the first magnetic other end portion is along the third direction,
the first opposing magnetic member includes a first opposing magnetic end portion and a first opposing magnetic other end portion, a direction from the first opposing magnetic end portion to the first opposing magnetic other end portion is along the third direction, and
a position of at least a part of the first magnetic element in the third direction is between a position of the first magnetic other end portion in the third direction and a position of the first opposing magnetic end portion in the third direction.

15. An inspection device, comprising
the magnetic sensor according to claim 1; and
a processor configured to process an output signal obtained from the magnetic sensor.

16. The sensor according to claim 1, further comprising:
a first substrate; and
a first insulating member,
the conductive layer being provided between the first substrate and the element portion, and
the first insulating member is provided between the conductive layer and the element portion.

17. The sensor according to claim 1, wherein a position of the first conductive member in the second direction is between a position of the conductive layer in the second direction and a position of the first magnetic element in the second direction.

18. A magnetic sensor, comprising:
an element portion including a first magnetic element, a second magnetic element, a first conductive member, and a second conductive member,
the first magnetic element including a first end portion and a first other end portion, a direction from the first end portion to the first other end portion being along a first direction,
the second magnetic element including a second end portion and a second other end portion, a direction from the second end portion to the second other end portion being along the first direction, the second end portion being electrically connected to the first other end portion,
the first conductive member including a first portion and a first other portion, the first portion corresponding to the first end portion, the first other portion corresponding to the first other end portion, and
the second conductive member including a second portion and a second other portion, the second portion corresponding to the second end portion, the second other portion corresponding to the second other end portion;

a conductive layer, a second direction from the conductive layer to the element portion crossing the first direction, the conductive layer including a first conductive portion and a first other conductive portion, a third direction from the first conductive portion to the first other conductive portion crossing a plane including the first direction and the second direction;
a first substrate; and
a first insulating member,
the conductive layer being provided between the first substrate and the element portion, and
the first insulating member is provided between the conductive layer and the element portion.

19. The sensor according to claim 18, further comprising a second insulating member,
the second insulating member being provided between the first insulating member and the element portion, and
the second insulating member fixing the element portion to the first insulating member.

20. The sensor according to claim 19, wherein
the element portion further includes a second substrate,
the second insulating member is provided between the first insulating member and the element portion, and
the second insulating member fixes the element portion to the first insulating member.

21. A magnetic sensor comprising:
an element portion including a first magnetic element, a second magnetic element, a first conductive member, and a second conductive member,
the first magnetic element including a first end portion and a first other end portion, a direction from the first end portion to the first other end portion being along a first direction,
the second magnetic element including a second end portion and a second other end portion, a direction from the second end portion to the second other end portion being along the first direction, the second end portion being electrically connected to the first other end portion,
the first conductive member including a first portion and a first other portion, the first portion corresponding to the first end portion, the first other portion corresponding to the first other end portion, and
the second conductive member including a second portion and a second other portion, the second portion corresponding to the second end portion, the second other portion corresponding to the second other end portion; and
a conductive layer, a second direction from the conductive layer to the element portion crossing the first direction, the conductive layer including a first conductive portion and a first other conductive portion, a third direction from the first conductive portion to the first other conductive portion crossing a plane including the first direction and the second direction;
wherein a position of the first conductive member in the second direction is between a position of the conductive layer in the second direction and a position of the first magnetic element in the second direction.

* * * * *